(12) United States Patent
Safe

(10) Patent No.: US 7,232,843 B2
(45) Date of Patent: Jun. 19, 2007

(54) COMPOSITIONS CONTAINING C-SUBSTITUTED DIINDOLYLMETHANE COMPOUNDS

(75) Inventor: Stephen S Safe, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 10/872,928

(22) Filed: Jun. 21, 2004

(65) Prior Publication Data

US 2004/0235929 A1 Nov. 25, 2004

Related U.S. Application Data

(63) Continuation of application No. 09/971,152, filed on Oct. 4, 2001.

(60) Provisional application No. 60/238,670, filed on Oct. 6, 2000, provisional application No. 60/238,675, filed on Oct. 6, 2000.

(51) Int. Cl.
*A61K 31/404* (2006.01)
*C07D 209/10* (2006.01)
(52) U.S. Cl. ..................... 514/414; 548/455
(58) Field of Classification Search .............. 548/455; 514/414
See application file for complete search history.

(56) References Cited

U.S. PATENT DOCUMENTS 5,948,808 A 9/1999 Safe

FOREIGN PATENT DOCUMENTS

WO WO 98/0357 11/1998

OTHER PUBLICATIONS

Kiang and Mann; Journal of Chemical Society, Abstracts 1953, 594. CAS Abstract Provided.*
Denis et al. Tet. Lett. 1997, 38(49), 8515-8518.*
Akgun et al. Journal of Heterocyclic Chemistry, 1983, 20(5), 1303-1305.*
Bergman et al. Tet. Lett. 1978, (42), 4051-4054. *CAS Bib Attached.*
Hill et al. J. Chem. Soc. Perkin Trans. 1, 1972, 9-10, 1210-19. *CAS Bib Attached.*
Noland et al. Journal of Organic Chemistry, 1961, 26, 4263-9.*
Bergman et al. Tetrahedron 1989, 45(17), 5549-64. *CAS Bib Attached.*
Chemical Abstracts, vol. 130, No. 16 (1999), Abstract No. 204767t, McDougal, A., et al. "*Methyl-substituted diindolylmethanes as AhR-based antitumorigenic/antiestrogenic compounds.*"
Chen, et al., "Aryl hydrocarbon receptor-mediated antiestrogenic and antitumorigenic activity of diindolylmethane," *Carcinogenesis*, 19:1631-1639 (1998).

Chen, et al., "Indole-3-carbinol and diindolylmethane as aryl hydrocarbon (Ah) receptor agonists and antagonists in T47D human breast cancer cells," *Biochem. Parmacol.* 51:1069-1076 (1996).
McDougal and Safe, "Methyl-substituted diindolylmethanes as AhR-based antitumorigenic/antiestrogenic compounds," *Organohalogen Compounds* 37:253-256 (1998).
McDougal, et al., "Inhibition of carcinogen-induced rat mammary tumor growth and other estrogen-dependant responses by symmetrical dihalosubstituted analogs of diindolylmethane," *Cancer Letts.* 151:169-179 (2000).
Michaud, et al., "Fruit and vegetable intake and incidence of bladder cancer in a male prospective cohort," *J. Natl. Cancer Inst.* 91:605-613 (1999).
Ramamoorthy, et al., "AhR-mediated antiestrogenicity of diindolylmethane and analogs *in vivo* and in vitro," *Organohalogen Compounds* 37:321-324 (1998).
Safe, "2,3,7,8-Tetrachlorodibenzo-*p*dioxin (TCDD) and related environmental antiestrogens: characterization and mechanism of action," *Endocrine Disrupters*, Naz (ed.), CRC Press, Boca Raton, Florida, pp. 187-221 (1999).
McDougal, et al., "Tamoxifen-induced antitumorigenic/antiestrogenic action synergized by a selective aryl hydrocarbon receptor modulator," *Cancer Res.* 61:3902-3907 (2001).
Safe, "Transcriptional activation of genes by 17 beta-estradiol through estrogen receptor-Sp1 interactions," *Vitam. Horm.* 62:231-252 (2001).
Safe, "Molecular biology of the Ah receptor and its role in carcinogenesis," *Toxicol. Lett.*120:1-7 (2001).
Sanderson, et al., "2,3,7,8-Tetrachlorodibenzo-p-dioxin and diindolylmethanes differentially induce cytochrome P450 1A1, 1B1 and 19 in H295R human adrenocortical carcinoma cells," *Toxicol Sci*. 61(1):40-48 (2001).
Chen, et al., "Identification of estrogen-induced genes downregulated by AhR agonists in MCF-7 breast cancer cells using suppression subtractive hybridization," *Gene* 262:207-214 (2001).
Wormke, et al., "Estrogen and aryl hydrocarbon receptor expression and crosstalk in human Ishikawa endometrial cancer cells," *J. Steroid Biochem. Mol. Biol.* 72(5):197-207 (2000).
Safe, et al., "Ah receptor agonists as endocrine disruptors: antiestrogenic activity and mechanisms," *Toxicol. Lett.* 102-103:343-7 (1998).
PCT International Search Report mailed Jul. 31, 2002, in PCT/US01/42519.

* cited by examiner

*Primary Examiner*—Kamal A. Saeed
*Assistant Examiner*—Jason M. Nolan
(74) *Attorney, Agent, or Firm*—Rick Matos; Innovar, L.L.C.

(57) ABSTRACT

Disclosed are methods and compositions for the treatment of a wide array of cancers and tumors. In illustrative embodiments, diindolylmethanes, C-substituted diindolylmethanes, and analogs thereof have been described, which when administered either alone, or in combination with other anti-cancer or anti-tumorigenic compounds, provide new therapies for the treatment of cancer.

34 Claims, 14 Drawing Sheets

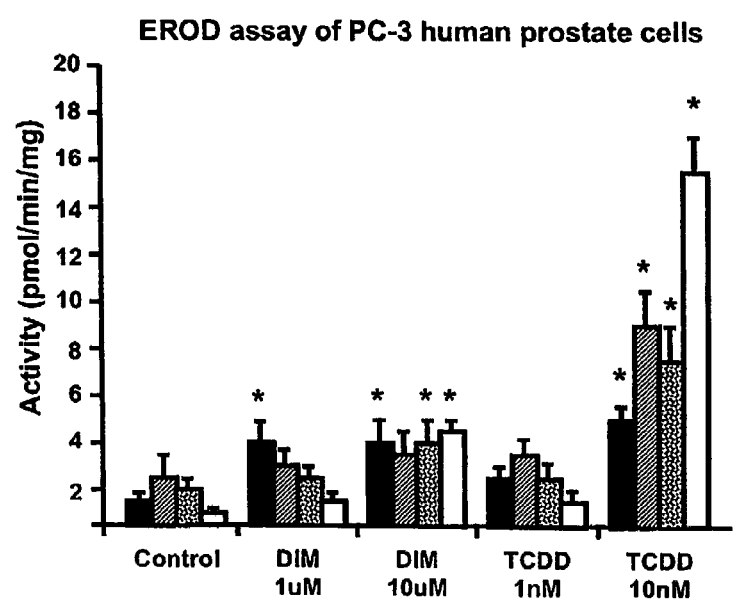
Figure 12    Induction of EROD activity by TCDD or DIM in PC3 prostate cancer cells: effects of concentration and treatment time.

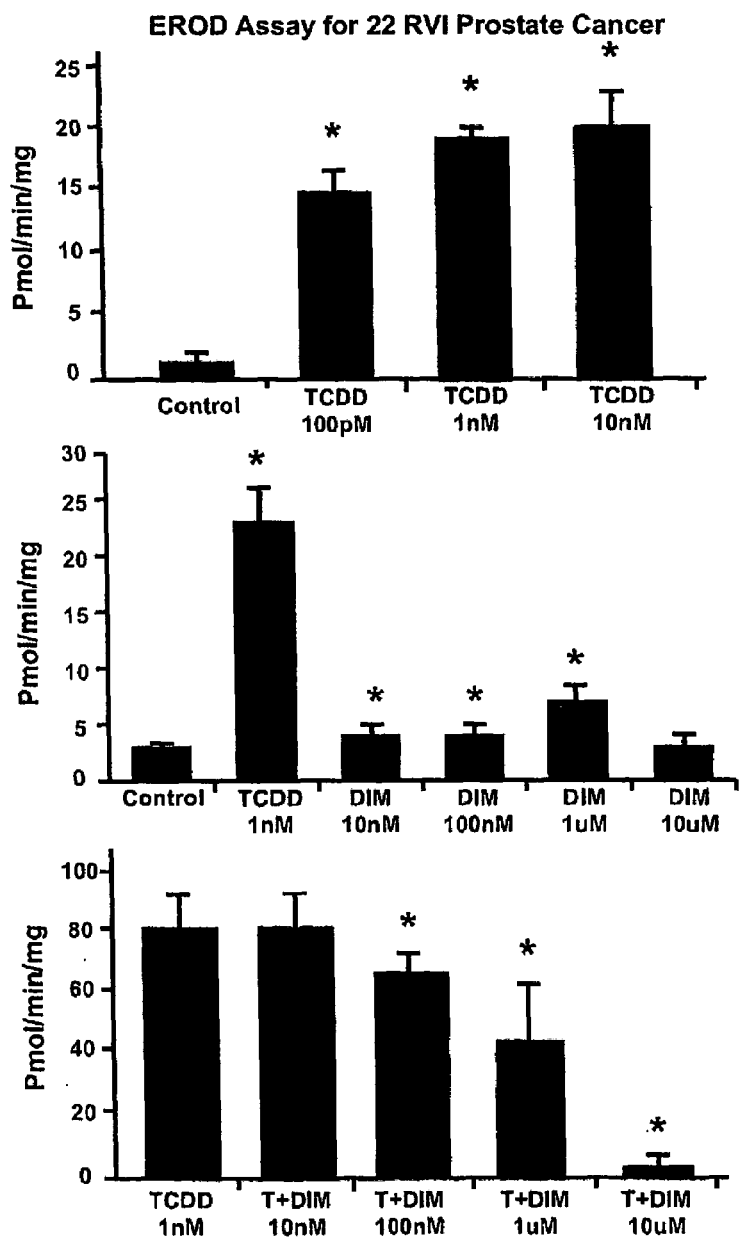
Figure 13  Induction of EROD activity in 22Rv1 prostate cancer cells after treatment with DIM or TCDD for 24 hr.

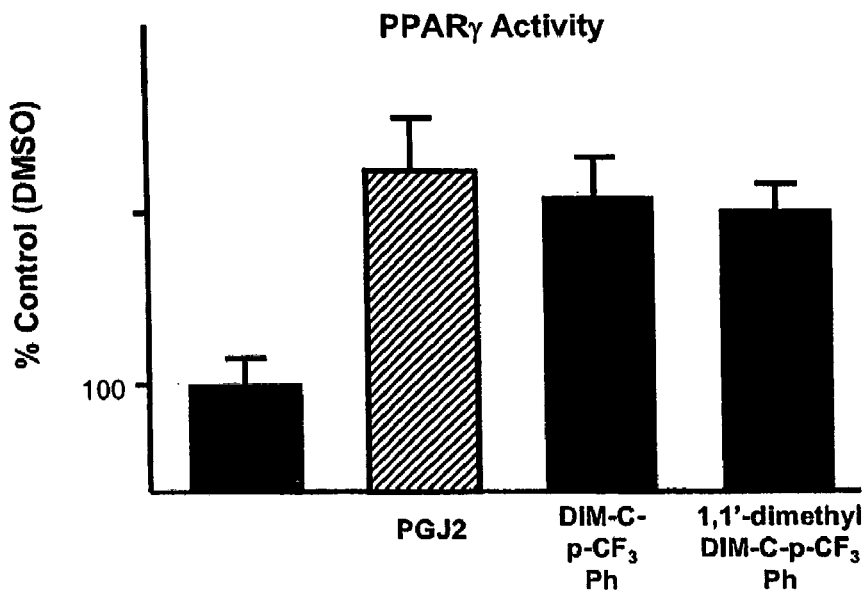
Figure 14   Induction of luciferase activity by 5 µM C-substituted DIMs and PGJ2 in MCF-7 breast cancer cells transfected with pGAL4$_5$ and pGAL4-PPARγ.
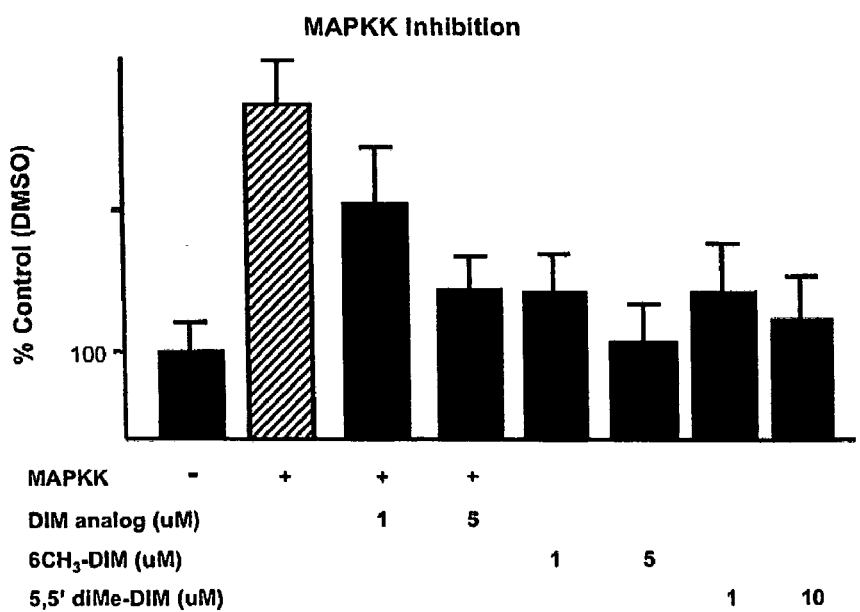
Figure 15   Induction of luciferase activity in cells transfected with pSRE, pMAPKK, and treated with DIMs.

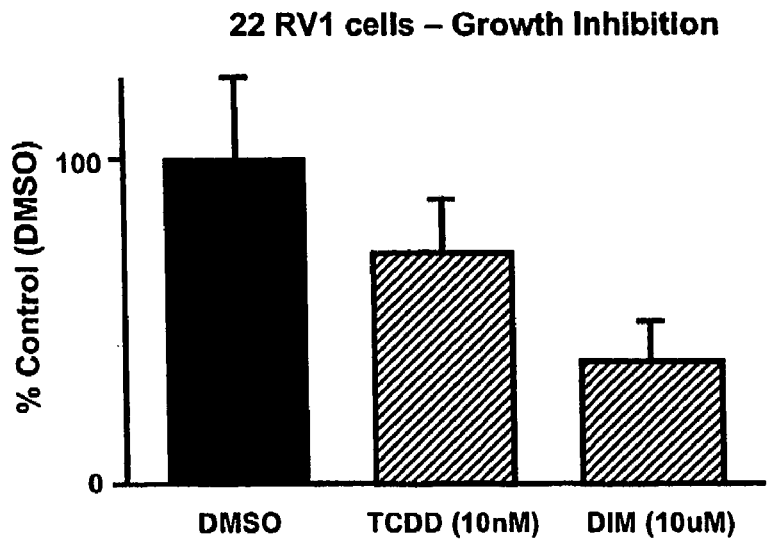
Figure 16　Inhibition of 22Rv1 prostate cancer cell growth by TCDD and DIM (6 days of growth in media containing 1% serum).
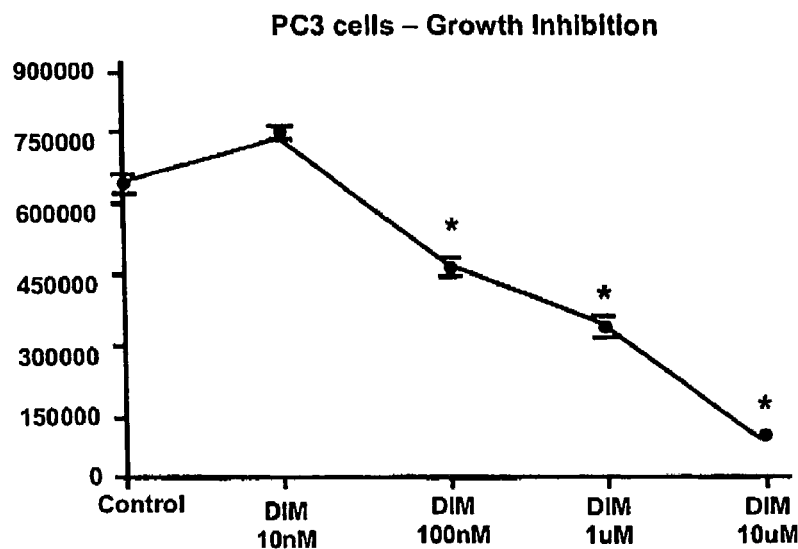
Figure 17　Inhibition of PC3 prostate cancer cell growth by DIM in cells grown in 1% serum for 6 days.

COMPOSITIONS CONTAINING C-SUBSTITUTED DIINDOLYLMETHANE COMPOUNDS

CROSS REFERENCE TO RELATED APPLICATIONS

This application is a continuation of U.S. patent application Ser. No. 09/971,152 filed Oct. 4, 2001, which claimed priority to U.S. Provisional Patent Applications Ser. Nos. 60/238,670 and 60/238,675, each filed on Oct. 6, 2000.

FIELD OF THE INVENTION

The invention relates generally to methods and compositions for the treatment of cancer. In particular, diindolylmethane, ring substituted diindolylmethane, C-substituted diindolylmethane, and analogs thereof that possess potent antiestrogenic and antitumorigenic activities are disclosed and used in anti-cancer applications.

BACKGROUND OF THE INVENTION

U.S. Pat. No. 5,516,790 (issued May 14, 1996) suggests a method of inhibiting estrogen activity by administering a biologically active amount of a substituted dibenzofuran or substituted dibenzodioxin.

U.S. Pat. No. 5,948,808 (issued Sep. 7, 1999) offers compounds and compositions of substituted indole-3-carbinols and diindolylmethane suitable for treating estrogen-dependent tumors along with methods of treating such cancerous-conditions.

U.S. Pat. No. 6,136,845 (issued Oct. 24, 2000) suggests methods and pharmaceutical combinations for inhibiting estrogen-dependent tumors via the co-administration of anti-estrogen triphenylethylenes, including tamoxifen and alkyl PCDFs.

Brockman, et al. ("Activation of PPARγ leads to inhibition of anchorage independent growth of human colorectal cancer cells" *Gastroenterology* 115:1049–1055, 1998) suggests that PPAR agonists will be effective antitumorigenic agents for treatment of colorectal cancer.

Chen, et al. ("Aryl Hydrocarbon receptor-mediated antiestrogenic and antitumorigenic activity of diindolylmethane," *Carcinogenesis*, 19:1631–1639, 1998) states that DIM represents a new class of relatively non-toxic AhR-based antiestrogens that inhibit E2-dependent tumor growth in rodents.

Chen, et al. ("Indole-3-carbinol and diindolylmethane as aryl hydrocarbon (Ah) receptor agonists and antagonists in T47D human breast cancer cells" *Biochem. Pharmacol.* 51:1069–1076, 1996) suggests that 2,3,7,8-tetrachlorodibenzo-p-dioxin (TCDD) induced CYP1A1-dependent ethoxyresorufin O-deethylase (EROD) activity in human breast cells, and co-treatment with TCDD plus different concentrations of I3C or DIM resulted in a significant decrease in the induced response at the highest concentration of I3C or DIM.

Duan, et al. ("Estrogen receptor-mediated activation of the serum response element in MCF-7 cells through MAPK-dependent phosphorylation of Elk-1" *J. Biol. Chem.* 276: 11590–11598, 2001) suggests that transcriptional activation of the serum response element by E2 was due to ERalpha activation of the MAPK pathway and increased binding of the serum response factor and Elk-1 to the serum response element.

Elstner, et al. ("Ligands for peroxisome proliferator-activated receptor gamma and retinoic acid receptor inhibit growth and induce apoptosis of human breast cancer cells in vitro and in BNX mice" *Proc. Natl. Acad Sci. USA* 95:8806–8811, 1998) suggests that combined administration of troglitazone and all-trans-retinoic acid causes prominent apoptosis and fibrosis of MCF7 tumors in triple immunodeficient mice without toxic effects on the mice.

Garcia, et al. ("Constitutive activation of Stat3 by the Src and JAK tyrosine kinases participates in growth regulation of human breast carcinoma cells" *Oncogene* 20:2499–2513, 2001) suggests that tyrosine kinases transduce signals through Stat3 protein that contribute to the growth and survival of human breast cancer cells in culture and potentially in vivo.

Jeng, et al. ("Role of MAP kinase in the enhanced cell proliferation of long term estrogen deprived human breast cancer cells" *Breast Cancer Res. Treat.* 62:167–175, 2000) suggests that the MAP kinase pathway is, in part, involved in the adaptive process which results in enhanced DNA synthesis and cell proliferation in the absence of exogenous estrogen in estradiol long term cells.

McDougal and Safe ("Methyl-substituted diindolylmethanes as AhR-based antitumorigenic/antiestrogenic compounds" *Organohalogen Compounds*, 37:253–256, 1998) suggests that methyl substituted DIMs inhibit estrogen induced breast cancer growth.

McDougal, et al. ("Inhibition of carcinogen-induced rat mammary tumor growth and other estrogen-dependent responses by symmetrical dihalo-substituted analogs of diindolylmethane" *Cancer Letts.*, 151:169–179, 2000) suggests that dihalo-substituted analogs of diindolylmethane significantly inhibited mammary tumor growth while no significant changes in organ weights or liver and kidney histopathology were observed.

Michaud, et al. ("Fruit and vegetable intake and incidence of bladder cancer in a male prospective cohort" *J. Natl. Cancer Inst.*, 91:605–613, 1999) suggests that high cruciferous vegetable consumption may reduce bladder cancer risk, but other vegetables and fruits may not confer appreciable benefits against this cancer.

Mueller, et al. ("Terminal differentiation of human breast cancer through PPAR" *Mol. Cell* 1:465–470, 1998) suggests that the PPAR gamma transcriptional pathway can induce terminal differentiation of malignant breast epithelial cells.

Ramamoorthy, et al. ("AhR-mediated antiestrogenicity of diindolylmethane and analogs in vivo and in vitro," *Organohalogen Compounds*, 37:321–324, 1998) suggests that DIM and substituted DIMs inhibit estrogen-induced uterine activities and breast cancer cell growth.

Safe ("2,3,7,8-Tetrachlorodibenzo-p-dioxin (TCDD) and related environmental antiestrogens: characterization and mechanism of action," in *Endocrine Disrupters*, Naz (ed.), CRC Press, Boca Raton, Fla., pp. 187–221, 1999) suggests that selective Ah receptor modulators (SahRMs) are effective inhibitors of mammary tumor growth with clinical potential for treatment of breast cancer.

Suh, et al. ("A new ligand for the peroxisome proliferator-activated receptor-PPAR, GW7845, inhibits rat mammary carcinogenesis" *Cancer Res.* 59:5671–5673, 1999) suggests the use of a ligand for peroxisome proliferator-activated receptor-gamma to prevent experimental breast cancer.

Tontonoz, et al. ("Terminal differentiation of human liposarcoma cells induced by ligands for peroxisome proliferator-activated receptor and the retinoid X receptor" *Proc. Natl. Acad. Sci. USA* 94:237–241, 1997) offers that PPAR gamma ligands such as thiazolidinediones and RXR-specific retinoids may be useful therapeutic agents for the treatment of liposarcoma.

Zhou, et al. ("Inhibition of murine bladder tumorigenesis by soy isoflavones via alterations in the cell cycle, apoptosis and angiogenesis" *Cancer Res.*, 58:5231–5238, 1998) suggests that soy isoflavones can inhibit bladder tumor growth through a combination of direct effects on tumor cells and indirect effects on the tumor neovasculature.

Cancer is one of the leading causes of premature death in most developed countries. Since 1990, more than five million people have died from various forms of cancer. Presently, many cancer treatments are ineffective, or display significant negative side effects. Thus, there exists a need for the development of new and more effective treatments of cancer.

SUMMARY OF THE INVENTION

Previous studies have demonstrated that diindolylmethane (DIM) and related compounds inhibit mammary tumor growth in experimental animals and also inhibit mammary and endometrial cancer cell proliferation in various in vitro models (Chen et al., 1998). DIM is formed from indole-3-carbinol (I3C) in the gut, and I3C and related compounds inhibit formation or growth of estrogen-regulated tumors in the rodent mammary, endometrium and uterus, suggesting that this compound may be acting as an antiestrogen. Results of ongoing studies with ring-substituted DIMs have demonstrated their potent antiestrogenic/antitumorigenic (patent submitted) activities. Research in this laboratory has focused on the antiestrogenic activity of aryl hydrocarbon receptor (AhR) agonists using 2,3,7,8-tetrachlorodibenzo-p-dioxin (TCDD) as a model compound (Safe, 1999). TCDD and related compounds inhibit mammary tumor growth in rodent models and 17β-estradiol (E2)-induced responses in the rodent uterus and human breast cancer cells. Subsequent research has shown that DIM and related compounds also bind the AhR, and mechanistic studies with DIM show that the antiestrogenic and antitumorigenic activities are also AhR-mediated, although this does not exclude other mechanisms of action.

Several studies have indicated that the diet can influence the process of carcinogenesis, and both fruit and vegetables are reported to possess antimutagenic and anticarcinogenic properties in human, animal and cell models. A recent study investigated the role of fruit and vegetable intake on bladder cancer risk in a male prospective cohort of 252 bladder cancer cases among 47,909 men enrolled in the Health Professionals Follow-up Study (Michaud et al., "Fruit and vegetable intake and incidence of bladder cancer in a male prospective cohort" *J. Natl. Cancer Inst.*, 91:605–613, 1999). A detailed analysis showed that there was a significant correlation between decreased bladder cancer risk and increased dietary intake of cruciferous vegetables suggesting that high cruciferous vegetable consumption may reduce bladder cancer risk. It was suggested that compounds such as the isothiocyanate sulforaphane (Michaud et al., "Fruit and vegetable intake and incidence of bladder cancer in a male prospective cohort" *J. Natl. Cancer Inst.*, 91:605–613, 1999) that induce phase 2 drug metabolizing enzymes may be chemoprotective.

Cruciferous vegetables including broccoli, cauliflower, Brussels sprouts, and cabbage contain several compounds such as indoles, isothiocyanates and dithiolthiones which modulate carcinogenesis in different animal models. For example, glucobrassicin (3-indolylmethyl glucosinolate), a major component of cauliflower (0.1 to 1.6 mmol/kg), cabbage (0.1 to 1.9 mmol/kg), and Brussels sprouts (0.5 to 3.2 mmol/kg) is readily converted to indole-3-carbinol (I3C). Therefore, it appears that DIM and related compounds may be not only chemopreventative, but also act as antitumorigenic agents for bladder and other cancers through the AhR and possibly other mechanistic pathways.

DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

| Figure | Description |
| --- | --- |
| 1 | Illustrates induced transformation of the rat hepatic cytosolic AhR and binding to [$^{32}$P]DRE in a gel mobility shift assays as described (Chen et al., 1998). Cytosol was treated with DMSO (lane 1), TCDD (lane 2), TCDD plus excess DRE (lane 3) or mutant DRE (lane 4). Lanes 5–13 were treated with the following compounds substituted at $R_8$ (note: $R_1/R_{1'}$ = $CH_3$ or H): $R_1/R_{1'}$ = $CH_3$, $R_8$ = p-$C_6H_4Cl$; $R_1/R_{1'}$, $R_8$ = $C_6H_4$—$C_6H_5$; $R_1/R_{1'}$, $R_8$ = $C_{10}H_7$ (naphthyl); $R_8$ = p$C_6H_4OH$; $R_1/R_{1'}$ = $CH_3$, $R_8$ = $C_6H_5OCH_3$; $R_1/R_{1'}$ = $CH_3$, $R_8$ = p$C_6H_4OH$; $R_8$ = p$C_6H_5OCH_3$; $R_8$ = $C_6H_4$—$C_6H_5$. |
| 2 | Illustrates the effects of C—PhDIM ($R_8$ = $C_6H_5$) and C—MeDIM ($R_8$ = Me) alone and in combination with 1 nM E2 on proliferation of MCF-7 human breast cancer cells. |
| 3 | Illustrates estrogenic and antiestrogenic activities of substitutes DIMs in T47D cells. Effects of different concentrations of substitutes DIMs alone or in combination with 1 nM E2 on cell proliferation was determined as described in Materials and Methods. Results are expressed as means ± SE for at least three replicate experiments for each treatment group. *Significant inhibition ($p < 0.05$) of E2-induced cell proliferation. The compounds used in this study include C—MeDIM ($R_8$ = $CH_3$), C—PhDIM ($R_8$ = $C_6H_5$), Nme—C—Ph—OHDIM ($R_1/R_{1'}$ = $CH_3$; $R_8$ = p-$C_6H_4OH$), and NMe—CPh—MeODIM ($R_1/R_{1'}$ = $CH_3$; $R_8$ = p-$C_6H_4OCH_3$). |
| 4 | Illustrates inhibition of DMBA-induced mammary tumor growth in female Sprague-Dawley rats. Rats were treated with C—PhDIM ($R_8$ = $C_6H_5$) (1.0 mg/kg/2 d) and tumor volumes in treated and control (corn oil) animals determined over a period of 21 days as described (McDouglas et al., 2000). |
| 5 | Illustrates inhibition of DMBA-induced mammary tumor growth in female Sprague-Dawley rats. Rats were treated with NMe—C—PhDIM ($R_1/R_{1'}$ = $CH_3$; $R_8$ = $C_6H_5$) (1.0 mg/kg/2 d) and tumor volumes in treated and control (corn oil) animals determined over a period of 21 days as described (McDouglas et al., 2000). |
| 6 | Illustrates inhibition of DMBA-induced mammary tumor growth in female and C—Ph—$CF_3$DIM ($R_8$ = p-$C_6H_4$—$CF_3$) (1.0 mg/kg/2 d) and tumor volumes in treated and control (corn oil) animals determined over a period of 21 days as described (McDouglas et al., 2000). |
| 7 | Illustrates inhibition of DMBA-induced mammary tumor growth in female Sprague-Dawley rats. Rats were treated with NMe—C—Ph—MeODIM ($R_1/R_{1'}$ = $CH_3$; $R_8$ = $C_6H_4OCH_3$), NMe—C—Ph—OHDIM ($R_1/R_{1'}$ = $CH_3$; $R_8$ = $C_6H_4OH$), and NMe—C-NaphthylDIM ($R_1/R_{1'}$ = $CH_3$; $R_8$ = $C_{10}H_7$) (1.0 mg/kg/2 d) and tumor volumes in treated and control (corn oil) animals determined over a period of 21 days as described (McDouglas et al., 2000). |
| 8 | Illustrates inhibition of DMBA-induced mammary tumor growth in female Sprague-Dawley rats. Rats were treated with NMe—BiPhDIM ($R_1/R_{1'}$ = $CH_3$; $R_8$ = $C_6H_4C_6H_5$), NMe—C—Ph—MeDIM ($R_1/R_{1'}$ = $CH_3$; $R_8$ = p-$C_6H_4CH_3$), and NMe—C—Ph—$CF_3$DIM (R/$R_{1'}$ = $CH_3$; $R_8$ = p-$C_6H_4CF_3$) (1.0 mg/kg/2 d) and tumor volumes in treated and control (corn oil) animals determined over a period of 21 days as described (McDouglas et al., 2000). |

-continued

Figure 1:
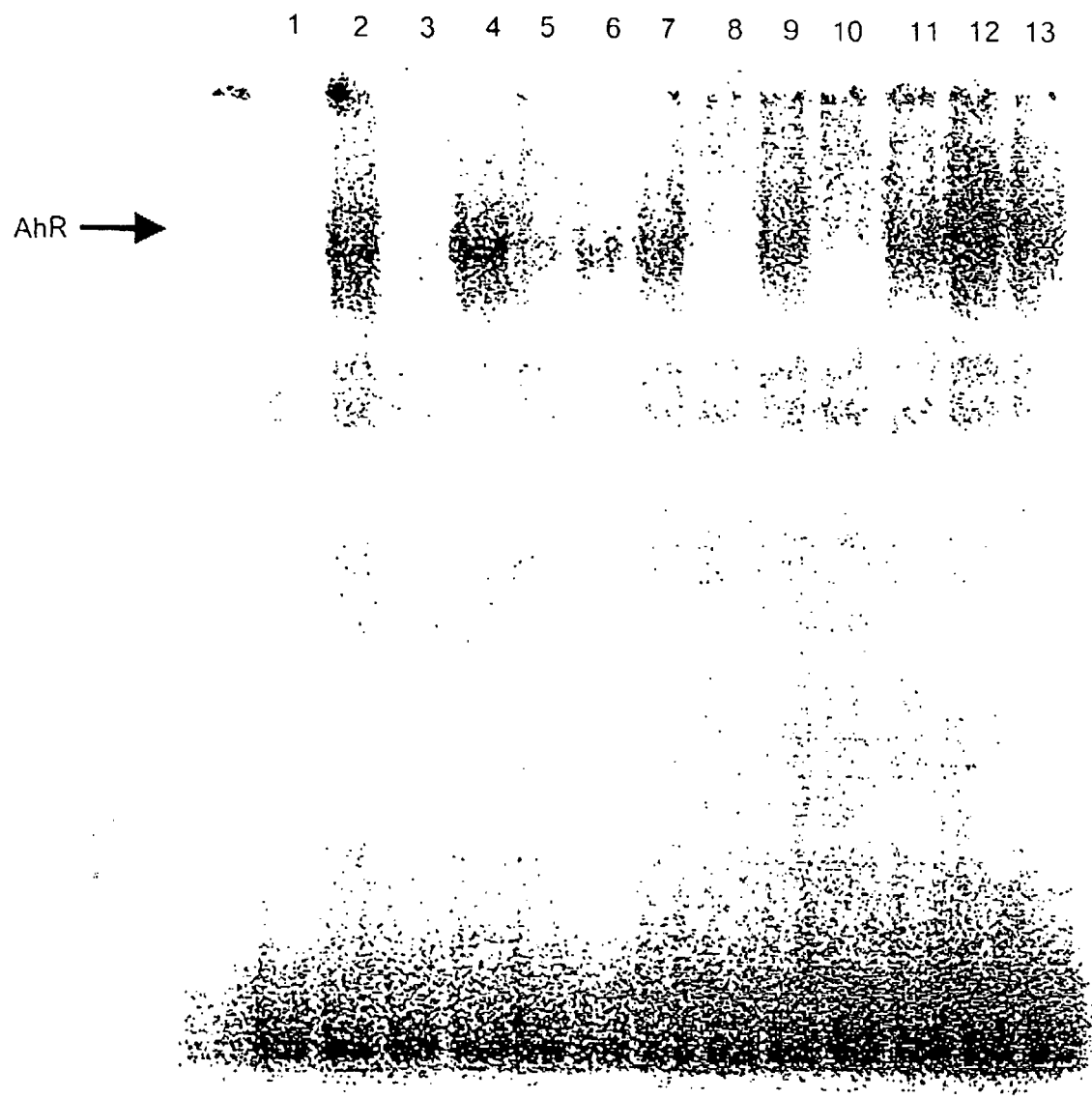

| Figure | Description |
|---|---|
| 9 | Illustrates comparative inhibition of TCCSUP bladder cancer cell growth by 0.1–50 µM genistein and DIM. |
| 10 | Depicts C-substituted diindolylmethane (DIM) compounds. |
| 11 | Depicts the overall scheme for the synthesis of C-substituted DIMs. |
| 12 | Induction of EROD activity of TCDD or DIM in PC3 prostate cancer cells: effects of concentration and treatment time. |
| 13 | Induction of EROD activity in 22Rv1prostate cancer cells after treatment with DIM or TCDD for 24 hrs. |
| 14 | Induction of luciferase activity by 5: M C-substituted DIMs and PG-J2 in MCF-7 breast cancer cells transfected with pGAL4$_5$ and pGAL4-PPAR(. |
| 15 | Induction of luciferase activity in cells transfected with pSRE, PMAPKK, and treated with DIMs. |
| 16 | Inhibition of 22Rv1 prostrate cancer cell growth by TCDD and DIM (6 days of growth in media containing 1% serum). |
| 17 | Inhibition of PC3 prostrate cancer cell growth by DIM in cells grown in 1% serum for 6 days. |

DEFINITIONS

The following definitions are provided in order to aid those skilled in the art in understanding the detailed description of the present invention.

"AhR" refers to aryl hydrocarbon receptor.
"DIM" refers to diindolylmethane.
"DMBA" refers to 7,12-dimethylbenz[a]anthracene.
"ER" refers to estrogen receptor.
"EROD" refers to ethoxyresorufin O-deethylase.
"E2" refers to 17β-estradiol.
"I3C" refers to indole-3-carbinol.
"MAPKK" refers to mitogen-activated protein kinase
"PPARγ" refers to peroxisome proliferator activity receptor γ.
"PCDF" refers to polycholorinated dibenzofuran.
"TCDD" refers to 2,3,7,8-tetrachlorodibenzo-p-dioxin.

DETAILED DESCRIPTION OF THE INVENTION

Provided in the present invention is a compound having the structure:

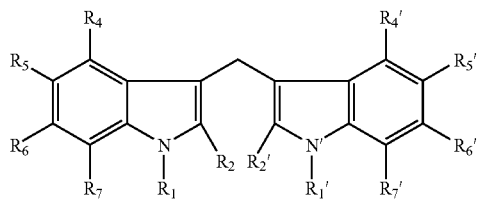

where $R_1$, $R_2$, $R_4$, $R_5$, $R_6$, $R_7$, $R_1'$, $R_2'$, $R_4'$, $R_5'$, $R_6'$, and $R_7'$, individually and independently, is hydrogen, or a substituent selected from the group consisting of a halogen, a nitro group, and a linear or branched alkyl or alkoxy group of about one to about ten carbons, preferably of about one to about five carbons, said compound having at least one substituent. The halogen is selected from the group consisting of chlorine, bromine, and fluorine. A compound such as this is referred to as a DIM derivative or a DIM analog.

In a preferred embodiment of the DIM derivatives, $R_1$, $R_2$, $R_4$, $R_6$, $R_7$, $R_1'$, $R_2'$, $R_4'$, $R_6'$, and $R_7'$ are hydrogen, $R_5$ and $R_5'$ are a halogen selected from the group consisting of chlorine, bromine and fluorine. Accordingly, preferred DIM derivatives include 5,5'-dichloro-diindolylmethane, 5,5'-dibromo-diindolylmethane, and 5,5'-difluoro-diindolylmethane.

Additional preferred DIM derivatives include compounds wherein $R_1$, $R_2$, $R_4$, $R_6$, $R_7$, $R_1'$, $R_2'$, $R_4'$, $R_6'$, and $R_7'$ are hydrogen, $R_5$ and $R_5'$ are an alkyl or alkoxyl having from one to ten carbons, and most preferably one to five carbons. These include, but are not limited to 5,5'-dimethyl-diindolylmethane, 5,5'-diethyl-diindolylmethane, 5,5'-dipropyl-diindolylmethane, 5,5'-dibutyl-diindolylmethane and 5,5'-dipentyl-diindolylmethane. These also include, but are not limited to, 5,5'-dimethoxy-diindolylmethane, 5,5'-diethoxy-diindolylmethane, 5,5'-dipropyloxy-diindolylmethane, 5,5'-dibutyloxy-diindolylmethane, and 5,5'-diamyloxy-diindolylmethane.

Additional preferred DIM derivatives include compounds wherein $R_2$, $R_4$, $R_5$, $R_6$, $R_7$, $R_2'$, $R_4'$, $R_5'$, $R_6'$, and $R_7'$ are hydrogen, $R_1$ and $R_1'$ are an alkyl or alkoxyl having from one to ten carbons, and most preferably one to five carbons. Such useful derivatives include, but are not limited to, N,N'-dimethyl-diindolylmethane, N,N'-diethyl-diindolylmethane, N,N'-dipropyl-diindolylmethane, N,N'-dibutyl-diindolylmethane, and N,N'-dipentyl-diindolylmethane.

In yet another preferred embodiment, $R_1$, $R_4$, $R_5$, $R_6$, $R_7$, $R_1'$, $R_4'$, $R_5'$, $R_6'$, and $R_7'$ are hydrogen, and $R_2$ and $R_2'$ are alkyl of one to ten carbons, and most preferably one to about five carbons. Such compounds include, but are not limited to, 2,2'-dimethyl-diindolylmethane, 2,2'-diethyl-diindolylmethane, 2,2'-dipropyl-diindolylmethane, 2,2'-dibutyl-diindolylmethane, and 2,2'-dipentyl-diindolylmethane.

In another embodiment, $R_1$, $R_2$, $R_4$, $R_6$, $R_7$, $R_1'$, $R_2'$, $R_4'$, $R_6'$, and $R_7'$ are hydrogen, and $R_5$ and $R_5'$ are nitro.

An alternative embodiment of the invention is directed towards DIM compounds with modifications at the bridge carbon ("C-substituted DIMs"). These compounds can be symmetrical or asymmetrical, depending on whether a single indole precursor is used in the synthesis (leading to a symmetrical C-substituted DIM, or if two different indole precursors were used (leading to an asymmetrical C-substituted DIM). The C-substituted DIMs are generally represented by the following structure:

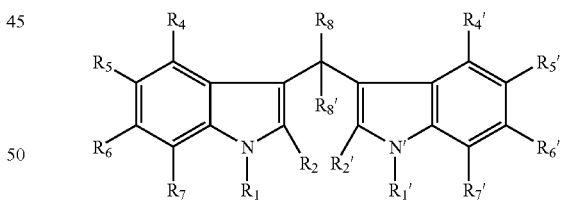

The scope of possible substituents at the $R_1$ through $R_7$ (and $R_1'$ through $R_7'$) are the same as described above in relation to DIMs. $R_8$ and $R_8'$ are each independently selected from the group consisting of hydrogen, a linear alkyl group containing one to about ten carbon atoms, a branched alkyl group containing one to about ten carbon atoms, a cycloalkyl group containing one to about ten carbon atoms, and an aryl group. At least one of $R_8$ and $R_8'$ are not hydrogen (if both $R_8$ and $R_8'$ are hydrogen, the compound is a DIM). A preferred embodiment of C-substituted DIMs includes when $R_1$, $R_2$, $R_1'$, and $R_2'$ are each individually hydrogen or methyl; $R_4$, $R_5$, $R_6$, $R_7$, $R_4'$, $R_5'$, $R_6'$, and $R_7'$ are each hydrogen; and $R_8$ and $R_8'$ are each individually hydrogen, methyl, $C_6H_5$, $C_6H_4OH$, $C_6H_4CH_3$, $C_6H_4CF_3$, $C_{10}H_7$, $C_6H_4C_6H_5$, or $C_6H_4OCH_3$. Depending on the nature of the two indole subunits, and of $R_8$ and $R_8'$, it is possible for the bridging carbon atom to be a chiral center (a carbon atom with four different substituents attached). If a chiral center exists, then the resulting C-substituted DIM would consist of two mirror image enantiomers, each of which is optically active. Resolution of the mixture using a chiral chromatography column or other means would result in the isolation of purified or pure enantiomer products. The different enantiomers may prove to have different biological activities.

The synthesis of the substituted I3C derivatives from the commercially-available substituted indoles is a convenient method for preparation of these compounds. The substituted DIM analogs can also be prepared by condensation of formaldehyde with substituted indoles; however, a disadvantage of the latter reaction is the formation of by-products which will complicate purification of the desired substituted DIM. The compounds of the present invention can be synthesized by dimethylformamide condensation of a suitable substituted indole to form a substituted indole-3-carboxaldehyde. Suitable substituted indoles include those indoles having substituents at $R_1$, $R_2$, $R_4$, $R_5$, $R_6$ and $R_7$ positions. These include, but are not limited to 5-methoxy, 5-chloro, 5-bromo, 5-fluoro, 5-methyl, 5-nitro, N-methyl, and 2-methyl indoles. The substituted indole 3-aldehyde product is treated with a suitable alcohol such a methanol and solid sodium borohydride to reduce the aldehyde moiety to give substituted I3Cs. Substituted DIMs are prepared by condensing the substituted indole-3-carbinol products. This may be achieved, for example, by treatment with a phosphate buffer having a pH of about 5.5. Use of a single indole starting material will lead to symmetrical products, while use of two different indole starting materials will lead to asymmetrical products.

The agents of the present invention may be administered topically, orally, by injection (IV, IP, IM), intranasally, transdermally, rectally, or by any means which delivers an effective amount of the active agent to the tissue or site to be treated. Suitable dosages are those which achieve the desired endpoint. It will be appreciated that different dosages may be required for treating different disorders. An effective amount of an agent is that amount which causes a significant decrease in neoplastic cell count, growth, or size.

Any of the above-described compounds can be used to treat cancer, either in vitro or in vivo. The cancer is generally any type of cancer, preferably adrenal cortical cancer, anal cancer, bile duct cancer, bone cancer, bone metastasis, brain cancer, cervical cancer, non-Hodgkin's lymphoma, rectum cancer, esophageal cancer, eye cancer, gallbladder cancer, gastrointestinal carcinoid tumors, gestational trophoblastic disease, Hodgkin's disease, Kaposi's sarcoma, kidney cancer, laryngeal and hypopharyngeal cancer, leukemia, liver cancer, lung cancer, lung carcinoid tumors, malignant mesothelioma, metastatic cancer, multiple myeloma, myelodysplastic syndrome, nasal cavity and paranasal cancer, nasopharyngeal cancer, neuroblastoma, oral cavity and oropharyngeal cancer, osteosarcoma, ovarian cancer, pancreatic cancer, penile cancer, pituitary cancer, retinoblastoma, salivary gland cancer, sarcoma, skin cancer, stomach cancer, testicular cancer, thymus cancer, thyroid cancer, uterine sarcoma, vaginal cancer, vulva cancer, Wilm's tumor and more preferably is bladder, colon or prostate cancer.

Those having ordinary skill in the art will be able to ascertain the most effective dose and times for administering the agents of the present invention, considering route of delivery, metabolism of the compound, and other pharmacokinetic parameters such as volume of distribution, clearance, age of the subject, and so on.

The active agents may be administered along with a pharmaceutical carrier and/or diluent. The agents of the present invention may also be administered in combination with other agents, for example, in association with other chemotherapeutic or immunostimulating drugs or therapeutic agents. Examples of pharmaceutical carriers or diluents useful in the present invention include any physiological buffered medium, i.e., about pH 7.0 to 7.4 comprising a suitable water soluble organic carrier. Suitable water soluble organic carriers include, but are not limited to corn oil, dimethylsulfoxide, gelatin capsules, and so on.

The present invention is exemplified in terms of in vitro and in vivo activity against various neoplastic and normal cell lines. The test cell lines employed in the in vitro assays are well recognized and accepted as models for antitumor activity in animals. The term "animals" as used herein includes, but is not limited to, mice, rats, domesticated animals such as, but not limited to cats and dogs, and other animals such as, but not limited to cattle, sheep, pigs, horses, and primates such as, but not limited to monkeys and humans. The mouse experimental tumor in vivo assays are also well recognized and accepted as predictive of in vivo activity in other animals such as, but not limited to, humans.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Synthesis of Diindolylmethane

Indole or ring-substituted indoles (e.g., 5-methoxy, 5-chloro, 5-bromo, 5-fluoro, 5-methyl, 5-nitro, N-methyl and 2-methyl) are commercially available and these compounds are used for synthesis of diindolylmethane analogs. Alkyl, substituted alkyl, aromatic, or substituted aromatic aldehydes (0.01 mole) are incubated with indole or a substituted indole (0.02 mole) in water (50 ml) plus glacial acetic acid (0.5 ml). Depending on the structure of the aldehyde or indole, the reaction is continued with stirring for 2 days to 2 weeks. The reaction product is either filtered or isolated by extraction with chloroform and the residue crystallized from benzene/petroleum spirit. The resulting substituted DIM is then used in in vivo or in vitro studies. DIMs tend to be photosensitive and should be stored in dark brown vials.

Example 2

Diindolylmethane Analogs as Antitumorigenic Agents for the Treatment of Multiple Cancers Initial studies used TCCSUP and J82 human bladder cancer cell lines that were maintained in RPMI culture media supplemented with 10% fetal bovine serum. Cell proliferation studies were carried out in multi-well plates, and compounds (in DMSO, 0.1% vol./vol.) were added and cell growth was determined over a period of 4–10 days. The growth inhibitory properties of DIM and related analogs were determined using the following prototypical compounds: DIM, 5,5'-dimethylDIM (5-Me-DIM), 2,2'-dimethylDIM (2-Me-DIM), and 5,5'-dichloroDIM (5-Cl-DIM) at concentrations from 0.1–10 µM. Proliferation of both human bladder cancer cell lines was significantly inhibited by all compounds used in this study; moreover, the more sensitive TCCSUP cells were inhibited by all compounds at the lowest concentration (0.1 µM) (FIG. 1). Interestingly, the DIM analogs were >100 times more inhibitory than genistein and related bioflavonoids in soy products that inhibited growth of these bladder cancer cells at 10 µM concentrations. These results suggest that DIM analogs exhibit excellent potential as inhibitors of bladder cancer since the soy products were also active as in vivo inhibitors of bladder cancer tumor growth.

Studies with HT-29 human colon cancer cells also indicate that DIM and related analogs protect against colon cancer. HT-29 cells were grown in DMEM and serum and treated with 25 µM DIM and 4,4'-dichloroDIM. After 72 hr, there was a 73 and 92% decrease in cell proliferation, respectively, and these antiproliferative effects could be observed with cell concentrations as low as 10 µM. These growth inhibitory effects were also accompanied by programmed cell death or apoptosis.

Example 3

PPAR(Activity of DIM Analogs

Peroxisome proliferator-activated receptor (PPAR) is a nuclear receptor that induces differentiation in multiple tissues and cell lines. Synthetic compounds that bind PPAR (inhibit growth, induce differentiation in multiple tumor cell lines, and inhibit mammary carcinogenesis in rodent models (Mueller et al., "Terminal differentiation of human breast cancer through PPAR" *Mol. Cell* 1:465–470, 1998; Elstner et al., "Ligands for peroxisome proliferator-activated receptor gamma and retinoic acid receptor inhibit growth and induce apoptosis of human breast cancer cells in vitro and in BNX mice" *Proc. Natl. Acad. Sci. USA* 95:8806–8811, 1998; Brockman et al., "Activation of PpaRg leads to inhibition of anchorage independent growth of human colorectal cancer cells" *Gastroenterology* 115:2049–1055, 1998; Tontonoz et al., "Terminal differentiation of human lipsarcoma cells induced by ligands for peroxisome proliferator-activated receptor and the retinoid X receptor" *Proc. Natl. Acad. Sci. USA* 94:237–241, 1997; Suh et al., "A new ligand for the peroxisome proliferator-activated receptor-PPAR, GW7845, inhibits rat mammary carcinogenesis" *Cancer Res*. 59:5671–5673, 1999). We have been investigating the potential role of DIMs as ligands for the PPARγ receptor using a chimeric protein containing the yeast GAL4 DNA binding domain fused to the PPARγ ligand binding domain (pGAL4-PPARγ). Ligand activation of pGAL4-PPARγ is detected using a construct containing five tandem GAL4 response elements (pGAL4$_5$) linked to a luciferase reporter gene. The results illustrated in FIG. 14 show that 5 µM 15-deoxy-$\gamma^{12,14}$-prostaglandin J$_2$ (PGJ) (a prototypical ligand for PPARγ induced a 2-fold increase in reporter gene activity in MCF-7 breast cancer cells, and similar results were obtained with 5 µM concentrations of DIM and 1,1'-dimethylDIM analogs containing C-substituted p-trifluoromethylphenyl substituents (FIG. 14). This suggests that substituted DIMs may also inhibit cancer growth through binding and activation of PPARγ, and we are currently investigating activities of other analogs in binding and functional assays.

Example 4

DIMs as Kinase Inhibitors

Many tumors overexpress growth factor receptors and other membrane receptors and exhibit activated kinase activities which contribute to the high rate of tumor growth (Garcia et al., "Constitutive activation of Stat3 by the Src and JAK tyrosine kinases participates in growth regulation of human breast carcinoma cells" *Oncogene* 20:2499–2513, 2001; Jeng et al., "Role of MAP kinase in the enhanced cell proliferation of long term estrogen deprived human breast cancer cells" *Breast Cancer Res. Treat*. 62:167–175, 2000). Therefore, we have been investigating the inhibitory effects of DIMs on kinase activities and our initial studies have examined inhibition of mitogen-activated protein kinase (MAPKK) which regulates expression of multiple genes involved in cell proliferation. MCF-7 cells are transfected with a constitutively active MAPKK expression plasmid (pMAPKK), and induction of activity is monitored through activation of the construct pSRE which contains a MAPKK-inducible serum response element (SRE) from the cfos protooncogene (Duan et al., "Estrogen receptor-mediated activation of the serum response element in MCF-7 cells through MAPK-dependent phosphorylation of Elk-1" *J. Biol. Chem*. 276:11590–11598, 2001). The results (FIG. 15) indicate that 1 or 5 µM concentrations of 5,5'- and 6,6'-dimethlyDIM inhibited MAPKK-induced activity suggesting that DIMs can also exhibit growth inhibitory properties in cancer cells by direct inhibition of kinase activity, and we are currently investigating inhibition of other growth related kinases by DIMs.

Example 5

Inhibition of Prostate Cancer Cell Growth

We examined the dose-dependent effects of DIM on proliferation of PC3 human prostate cancer cells in culture, and the results (FIG. 16) showed that in DIM (100 nM–10 µM) significantly inhibited growth of this cell lines in 1% serum. In a second study using 22Rv1 human prostate cancer cells, both 1 nM TCDD (an Ah receptor ligand) and 10 µM DIM inhibited proliferation of this cell line, thus confirming the anticancer activity of DIMs on prostate cancer cells.

Example 6

Synthesis of C-Substituted DIMs

Figure 11:
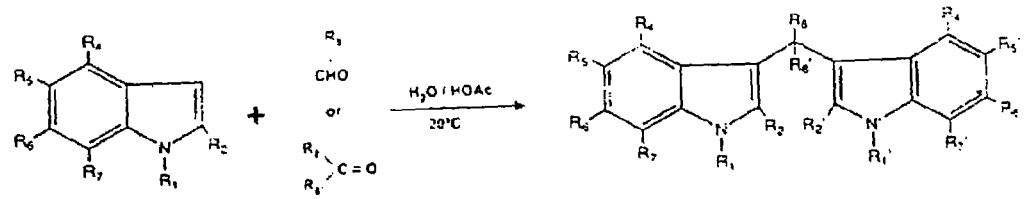

The overall scheme for synthesis of C-substituted DIMs is shown in FIG. 11. A substituted indole (10 mmol) containing one or more substituents ($R_1$–$R_7$) is incubated with a slight molar excess of a substituted aldehyde ($R_8$—CHO, 10 mmol) or ketone in 50 ml water and 0.6 ml glacial acetic acid. The mixture is stirred rapidly for 1–30 days, and the formation of DIM condensation product is monitored by gas-liquid or thin-layer chromatography. After the reaction is complete, the condensation mixture is filtered, washed with distilled water, dried and crystallized from benzene or benzene/petroleum spirit to give a pure condensation product. The reaction products may be light sensitive and should be synthesized and stored in the dark. In addition, unsymmetrical condensation products using different substituted indoles can also be synthesized, purified and separated by high performance liquid chromatography for biological screening. In addition, symmetrical or unsymmetrical ketones ($R_8$, $R_8'$ C=O) can be used to give additional substituted DIMs at the bridged carbon atoms.

Figure 10:
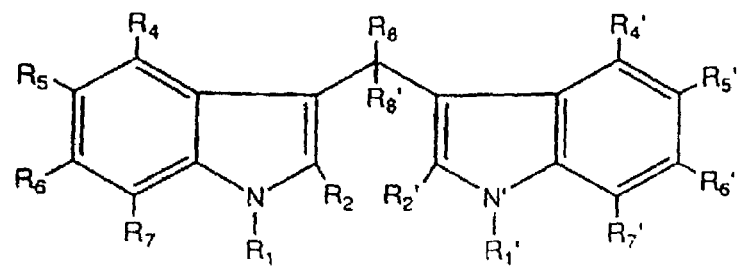

C-substituted diindolylmethanes (DIMs) include the generalized set of compounds shown in FIG. 10, where $R_8/R_8'$ are substituents at the C-bridge, and $R_1/R_1'$-$R_7/R_7'$ are substituents at positions 1, 2, 4, 5, 6 and 7. Table 1 illustrates a range of prepared compounds.

investigated the induction of EROD activity by TCDD in androgen-responsive LnCAP prostate cancer cells and there was also significant induction of EROD activity. Thus, human prostate cancer cells express a functional Ah receptor.

Studies have demonstrated that DIM and ring-substituted DIM analogs exhibit antiestrogenic activities in breast cancer cells and antitumorigenic activity in the carcinogen-induced rat mammary tumor model (Chen et al., "Aryl Hydrocarbon receptor-mediated antiestrogenic and antitumorigenic activity of diindolylmethane," Carcinogenesis, 19:1631–1639, 1998; McDougal et al., "Inhibition of carcinogen-induced rat mammary tumor growth and other

TABLE 1

| $R_1$ | H, $CH_3$ | H, $CH_3$ | H, $CH_3$ | H,$CH_3$ | H, $CH_3$ | H, $CH_3$ | H, $CH_3$ | H, $CH_3$ | H, $CH_3$ |
|---|---|---|---|---|---|---|---|---|---|
| $R_{2,4-7}$ | H | H | H | H | H | H | H | H | 2-$CH_3$ |
| $R_8$ | $CH_3$ | $C_6H_5$ | $C_6H_4$—OH | $C_6H_4$—$CH_3$ | $C_6H_4$—$CF_3$ | $C_{10}H_7$ | $C_6H_4$—$C_6H_5$ | $C_6H_4$—$OCH_3$ | $CH_3$ |

All possible substituents on the ring (i.e., more than one $R_{1,2,4-7}$ as well as different substituents on both rings, i.e., unsymmetrical substitution) and at the bridge C-atom [i.e., one or two bridge substituents ($R_8/R_{8'}$)] that may be the same or different.

Example 7

AhR Activities

The DIM series of compounds containing both ring and methylene-C substituents can be used for treating multiple cancers through both Ah receptor-dependent and -independent pathways. Many of these compounds bind the Ah receptor; however, it is suspected that they may also inhibit tumor growth by other mechanisms, such as through activation of PPARγ (Example 3). Results illustrated below summarize the concentration-dependent induction of CYP1A1-dependent ethoxyresorufin O-deethylase (EROD) activity by DIM and TCDD in androgen-nonresponsive PC3 human prostate cancer cells (FIG. 12). Initial studies showed that minimal (but significant) induction was observed after 24 hours; however, 10 μM DIM and 10 nM TCDD induced EROD activity which was maximal (for TCDD) after treatment for 96 hours. The fold-induction response for DIM was lower than observed for TCDD even at concentrations of DIM that were 1000 times higher than TCDD, and this response is typical for SahRMs such as DIM which exhibit low Ah receptor-mediated toxicities (Chen et al., "Indole-3-carbinol and diindolylmethane as aryl hydrocarbon (Ah) receptor agonists and antagonists in T47D human breast cancer cells" Biochem. Pharmacol 51:1069–1076, 1996). We also investigated the induction of EROD activity in two additional androgen-responsive prostate cancer cell lines. The results illustrated in FIG. 13 show that 0.1 to 10 nM TCDD induced EROD activity in androgen-responsive 22 Rv1 prostate cancer cells (top), and DIM also induced a minimal (but significant) increase in EROD activity (middle). In combination studies, higher concentration of DIM inhibited TCDD induced activity, and this is consistent with results of previous studies which show that DIM interacts directly with CYP1A1 protein and inhibits catalytic activity such as EROD (Chen et al., "Indole-3-carbinol and diindolylmethane as aryl hydrocarbon (Ah) receptor agonists and antagonists in T47D human breast cancer cells" Biochem. Pharmacol. 51:1069–1076, 1996). We have also estrogen-dependent responses by symmetrical dihalo-substituted analogs of diindolylmethane" Cancer Letts., 151: 169–179, 2000). However, the activities of the C-substituted analogs have not been determined. Moreover, it might be expected that C-substitution with alkyl, phenyl or other aromatic substituents would decrease binding affinity to the Ah receptor and render these compounds inactive as Ah receptor based antiestrogens. Results of preliminary studies with some C-substituted DIMs indicated that most of these compounds only weakly induce transformation of the rat cytosolic Ah receptor suggesting that they exhibit some Ah receptor-like activity (FIG. 1).

Studies indicate that a few of the substituted DIMs also transcriptionally activate peroxisome proliferator activity receptor γ (PPARγ) (Example 3) and some PPARγ agonists also inhibit carcinogen-induced mammary tumor growth.

Example 8

In Vitro Studies with Breast Cancer Cells

Figure 2:
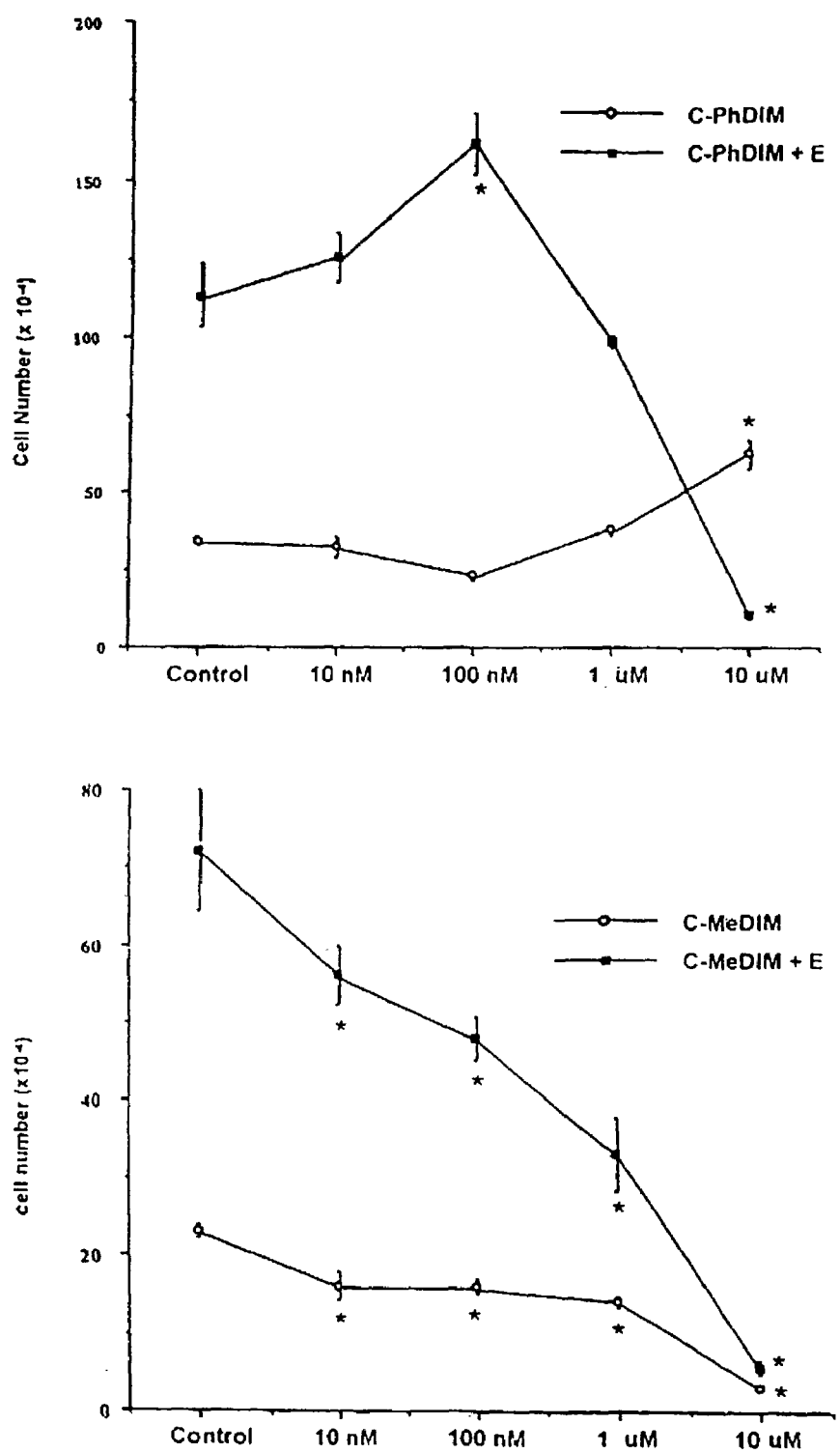
Figure 3:
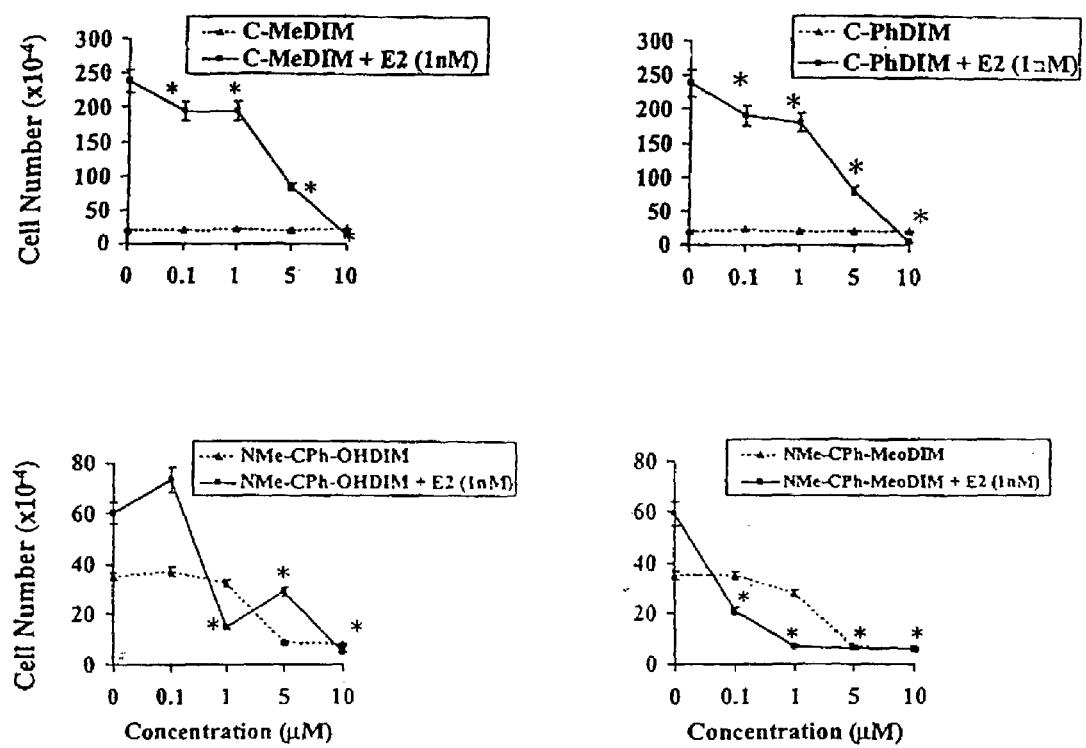

Previous studies have demonstrated that DIM and substituted DIMs inhibited estrogen-induced growth of breast cancer cells in culture (Chen et al., "Aryl Hydrocarbon receptor-mediated antiestrogenic and antitumorigenic activity of diindolylmethane," Carcinogenesis, 19:1631–1639, 1998; McDougal et al., "Inhibition of carcinogen-induced rat mammary tumor growth and other estrogen-dependent responses by symmetrical dihalo-substituted analogs of diindolylmethane" Cancer Letts., 151:169–179, 2000) and these studies have also been carried out with C-substituted DIMs. The results in FIG. 2 summarize the antiestrogenic activity of two C-substituted DIMs wherein $R_8$=$CH_3$ (methyl) or $C_6H_5$ (phenyl) and $R_1$–$R_8$=H. The results show that at concentrations up to 10 μM, the compounds alone do not affect growth of MCF-7 breast cancer cell lines. However, in cells co-treated with 1 nM estradiol (E2) plus different concentrations of the C—$CH_3$ or C—$C_6H_5$ substituted DIMs, there was significant inhibition of E2-induced cell proliferation. In a separate study, it was also shown that the same compounds and other C-substituted DIMs were also antiestrogenic in T47D cells, and these include the C-p-phenol and C-p-anisole compounds in which $R_1$=$CH_3$ (methyl) (i.e., NMe-CPh-OHDIM and NMe-CPh-MeODIM, respectively) (FIG. 3).

Example 9

In Vivo Antitumorigenic Activity of C-Phenyl Substituted DIM in the DMBA-Induced Rat Mammary Tumor Model Several studies have previously demonstrated that AhR agonists exhibit antiestrogenic activity in both in vivo and in vitro models (Chen et al.,"Aryl Hydrocarbon receptor-mediated antiestrogenic and antitumorigenic activity of diindolylmethane," *Carcinogenesis*, 19:1631–1639, 1998; McDougal et al., "Inhibition of carcinogen-induced rat mammary tumor growth and other estrogen-dependent responses by symmetrical dihalo-substituted analogs of diindolylmethane" *Cancer Letts.*, 151:169–179, 2000). Research has identified a series of alternate substituted alkyl polychlorinated dibenzofurans (PCDFs) that bind to the AhR, exhibit low toxicity but are relatively potent antiestrogens in both in vivo and in vitro studies (Safe, "2,3,7,8-Tetrachlorodibenzo-p-dioxin (TCDD) and related environmental antiestrogens: characterization and mechanism of action," in *Endocrine Disrupters*, Naz (ed.), CRC Press, Boca Raton, Fla., pp. 187–221, 1999). These compounds inhibit mammary tumor growth in female Sprague-Dawley rats initiated with 7,12-dimethylben[a]anthracene (DMBA) and the antitumorigenic activities of alkyl PCDFs are not accompanied by any apparent liver or extrahepatic toxic effects. Comparable studies have been carried out using DIM and ring-substituted DIMs, and these compounds are also relatively nontoxic Ah receptor-based antiestrogens that block mammary tumor growth in vivo (Chen et al., "Aryl Hydrocarbon receptor-mediated antiestrogenic and antitumorigenic activity of diindolylmethane," *Carcinogenesis*, 19:1631–1639, 1998; McDougal et al.,"Inhibition of carcinogen-induced rat mammary tumor growth and other estrogen-dependent responses by symmetrical dihalo-substituted analogs of diindolylmethane" *Cancer Letts.*, 151: 169–179, 2000).

Figure 4:
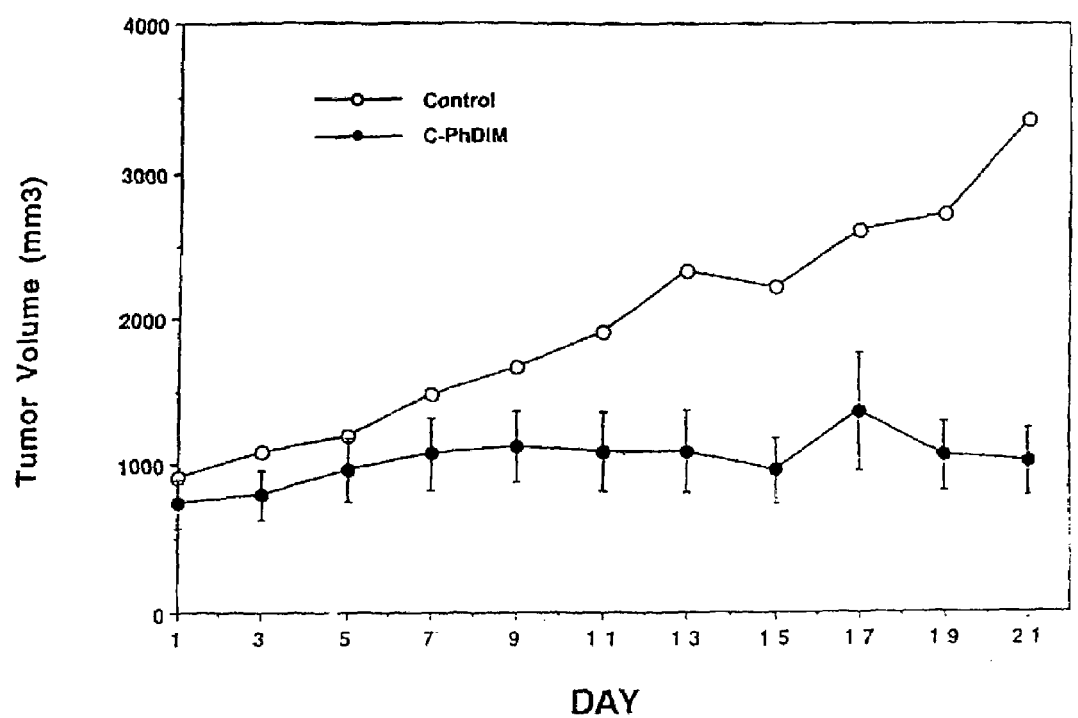

FIG. 4 illustrates the potent inhibition of mammary tumor growth by C-PhDIM ($R_8=C_6H_5$) in DMBA-induced Sprague-Dawley rats. The anticarcinogenic response was observed at a dose of 1.0 mg/kg every 2 days and as shown in Table 2, this was not accompanied by changes in body/organ weights or altered tissue histopathology.

TABLE 2

Antitumorigenic activity of C-PhenylDIM in female Sprague-Dawley Rats

|  | Control | C-PhenylDIM |
|---|---|---|
| Tumor volume (mm³) | 3332 ± 701 | 1025 ± 245* |
| Tumor weight (g) | 5.90 ± 2.0 | 1.40 ± 0.4* |
| EROD (pmol/mg/min) | 448 ± 170 | 309 ± 102 |
| Liver (% body weight) | 3.1 ± 0.2 | 3.2 ± 0.1 |
| Uterus (% body weight) | 0.15 ± 0.02 | 0.19 ± 0.02 |
| Heart (% body weight) | 0.25 ± 0.01 | 0.38 ± 0.03 |
| Spleen (% body weight) | 0.30 ± 0.03 | 0.33 ± 0.05 |
| Kidney (% body weight) | 0.32 ± 0.01 | 0.33 ± 0.01 |

*Significantly different from control values ($p < 0.05$ by ANOVA and Duncan's New Multiple Range).

Figure 5:
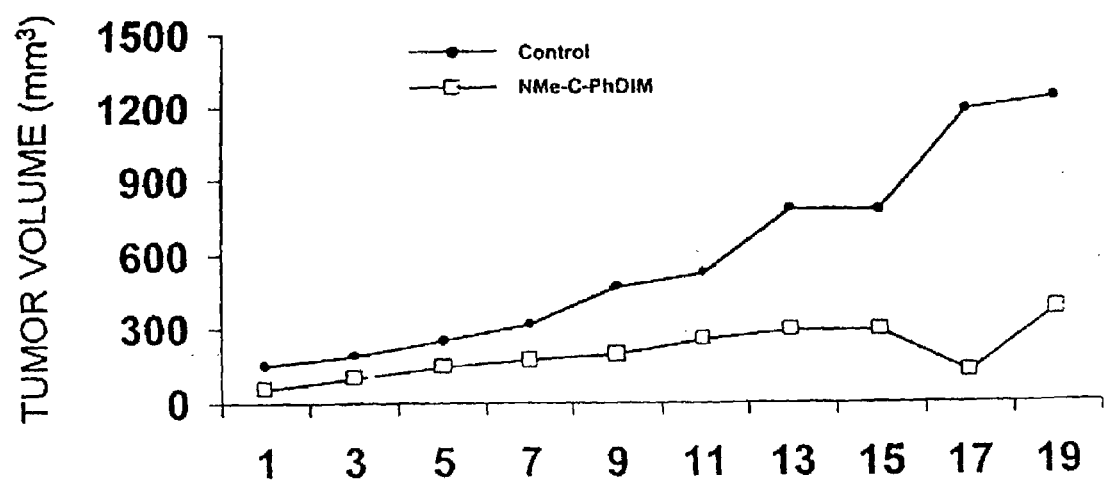
Figure 6:
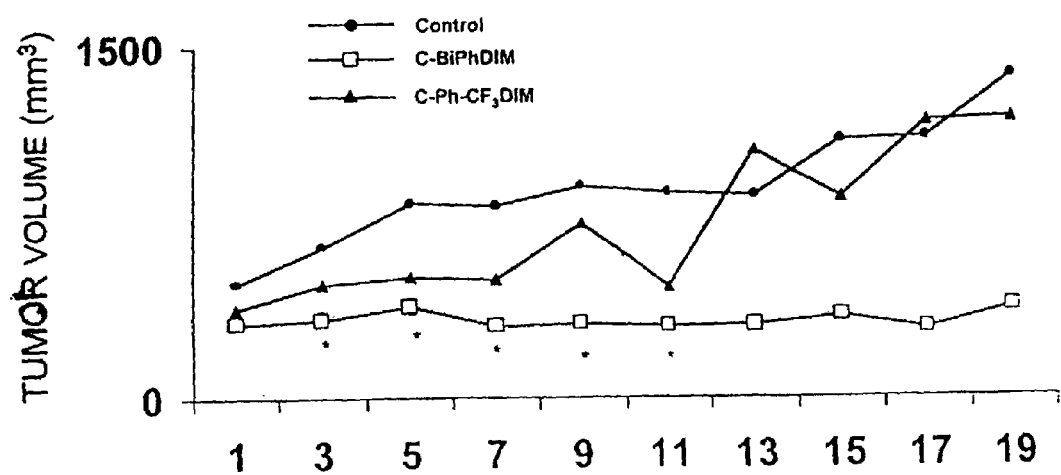
Figure 7:
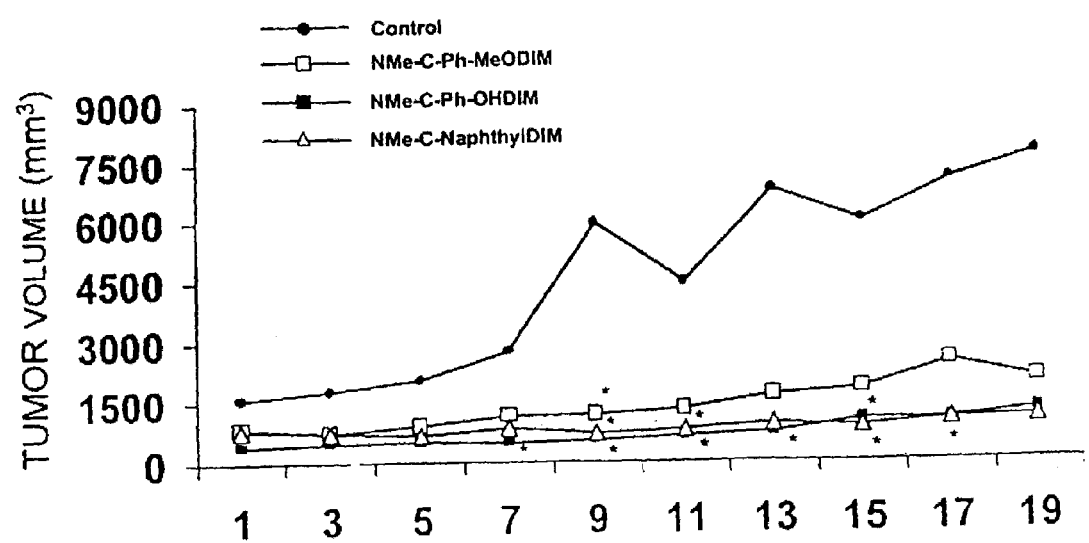
Figure 8:
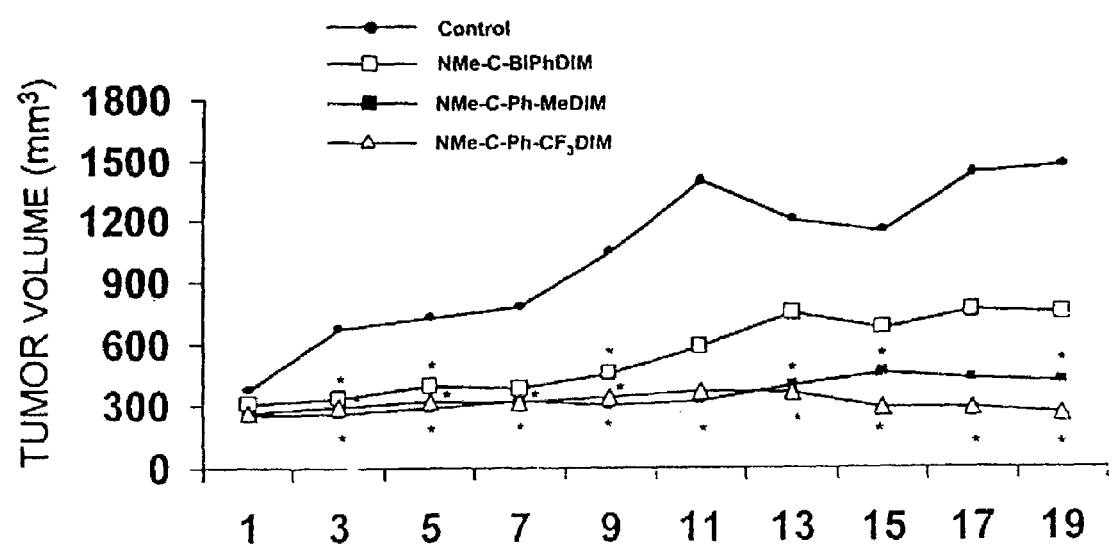

Similar results have been observed for other C-substituted DIMs including NMe-C-PhDIM ($R_1/R_{1'}=CH_3$; $R_8=C_6H_5$; other R groups=H) (FIG. 5); C-BiphDIM ($R_8=C_6H_4$—$C_6H_5$; all other R groups=H) (FIG. 6); NMe-C-Ph-MeODIM ($R_1/R_{1'}=CH_3$; $R_8=C_6H_4$—OMe; all other R groups=H); NMe-C-PhOHDIM ($R_1/R_{1'}=CH_3$; $R_8=C_6H_4OH$; all other R groups=H); NMe-C-NaphthylDIM ($R_1/R_{1'}=CH_3$; $R_8=C_{10}H_7$ (naphthyl); all other R groups=H (FIG. 7); NMe-C-BiphDIM ($R_1/R_{1'}=CH_3$; $R_8=C_6H_4$—$C_6H_5$; all other R groups=H); NMe-C-PhMeDIM ($R_1/R_{1'}=CH_3$; $R_8=C_6H_4$—$CH_3$; other R groups=H); NMe-C-Ph-$CF_3$DIM ($R_1/R_{1'}=CH_3$; $R_8=C_6H_4CF_3$; other R groups=H). All of these studies were carried out in DMBA-induced rats as described (McDougal et al., "Inhibition of carcinogen-induced rat mammary tumor growth and other estrogen-dependent responses by symmetrical dihalo-substituted analogs of diindolylmethane" *Cancer Letts.*, 151:169–179, 2000) and at doses of 1 or 5 mg/kg every second day.

The inventors hypothesize that DIM and related compounds may be not only chemopreventative, but also act as antitumorigenic agents for bladder and other cancers through the AhR and possibly other mechanistic pathways.

Figure 9:
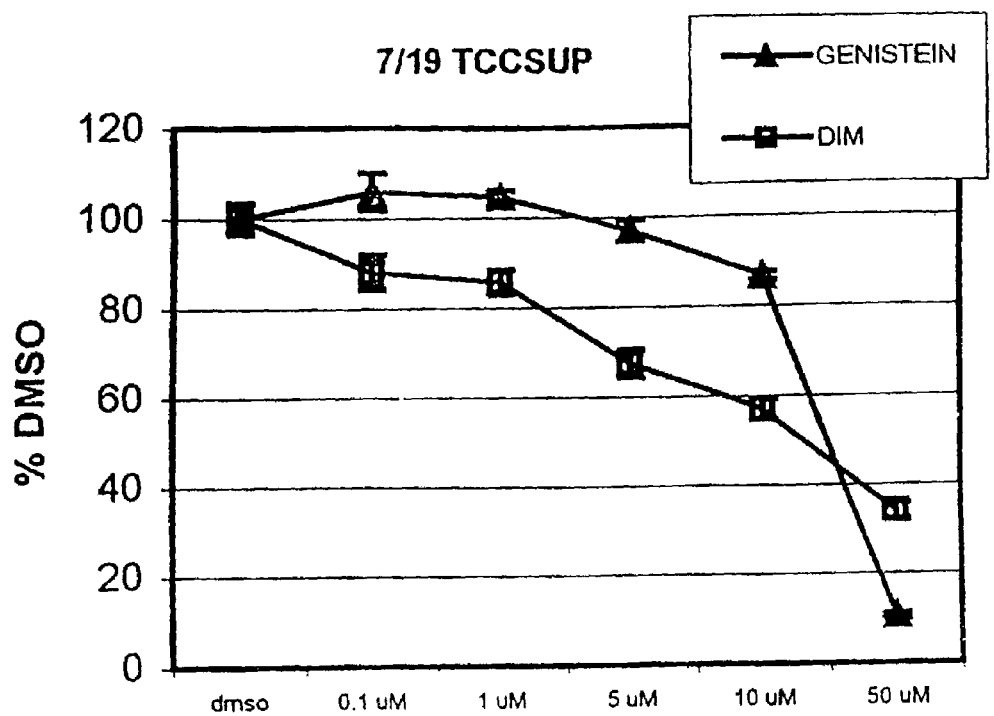

Initial studies on the possible protective role for DIM compounds in bladder cancer used TCCSUP and J82 human bladder cancer cell lines that were maintained in RPMI culture media supplemented with 10% fetal bovine serum. Cell proliferation studies were carried out in multi-well plates, and compounds (in DMSO, 0.1% vol./vol.) were added and cell growth was determined over a period of 4–10 days. The growth inhibitory properties of DIM and related analogs were determined using the following prototypical compounds: DIM, 5,5'-dimethylDIM (5-Me-DIM), 2,2'-dimethylDIM (2-Me-DIM), and 5,5'-dichloroDIM (5-Cl-DIM) at concentrations from 0.1–10 μM. Proliferation of both human bladder cancer cell lines was significantly inhibited by all compounds used in this study; moreover, the more sensitive TCCSUP cells were inhibited by all compounds at the lowest concentration (0.1 μM) (FIG. 9). Interestingly, the DIM analogs were more inhibitory than genistein and related bioflavonoids in soy products that inhibited growth of these bladder cancer cells at 10 μM concentrations. In vivo studies show that genistein and related soy products inhibit mouse bladder carcinogenesis (Zhou et al.,"Inhibition of murine bladder tumorigenesis by soy isoflavones via alterations in the cell cycle, apoptosis and angiogenesis" *Cancer Res.*, 58:5231–5238, 1998) suggesting that the DIMs will also be antitumorigenic for bladder cancer. These results suggest that DIM analogs exhibit excellent potential as inhibitors of bladder cancer since the soy products were also active as in vivo inhibitors of bladder cancer tumor growth.

Preliminary studies with HT-29 human colon cancer cells also indicate that DIM and related analogs protect against colon cancer. HT-29 cells were grown in DMEM and serum and treated with 25 μM DIM and 4,4'-dichloroDIM. After 72 hours, there was a 73 and 92% decrease in cell proliferation, respectively, and these antiproliferative effects could be observed with concentrations as low as 10 μM. These growth inhibitory effects were also accompanied by programmed cell death, or apoptosis.

These cell culture and in vivo results demonstrate that DIM compounds also inhibit growth of multiple tumor cells indicating a broader application for the DIM compounds in cancer chemotherapy.

The inventors previously described the combined use of Ah receptor-based alkyl PCDFs with clinically-used ER antagonists such as tamoxifen, and contemplate that in the present disclosure the use of both C- and ring-substituted DIMs in combination treatment with ER antagonists such as tamoxifen may provide one example of a combined therapy approach to the treatment of breast cancer. Previous studies have demonstrated that DIM and ring-substituted DIM analogs exhibit antiestrogenic activities in breast cancer cells and antitumorigenic activity in the carcinogen-induced rat mammary tumor model. However, the activities of the C-substituted analogs have not been determined. Moreover, it might be expected that C-substituted with alkyl, phenyl or other aromatic substituents would decrease binding affinity to the Ah receptor and render these compounds inactive as Ah receptor-based antiestrogens.

Several studies have previously demonstrated that AhR agonists exhibit antiestrogenic activity in both in vivo and in vitro models. Research in this laboratory has identified a series of alternate substituted alkyl polychlorinated dibenzofurans (PCDFs) which bind to the AhR, exhibit low toxicity but are relatively potent antiestrogens in both in vivo and in vitro studies. These compounds inhibit mammary tumor growth in female Sprague-Dawley rats initiated with 7,12-dimethylbenz[a]-anthracene (DMBA) and the antiturnorigenic activities of alkyl PCDFs are not accompanied by any apparent liver or extrahepatic toxic effects. Comparable studies have been carried out using DIM and ring-substituted DIMs (patent application pending) and these compounds are also relatively nontoxic Ah receptor-based antiestrogens that block mammary tumor growth in vivo.

Surprisingly, the C-substituted DIMs retained their binding affinity for the Ah receptor and $IC_{50}$ competitive binding values of $1.1 \times 10^{-8}$, $9.8 \times 10^{-8}$, $5.5 \times 10^{-10}$, and $1.8 \times 10^{-9}$ M have been observed for the C-methyl, C-phenyl, 1-methyl/C-p-chlorophenyl and 1-methyl/C-biphenyl substituents, respectively.

In addition, it has been demonstrated that several C-substituted DIMs exhibit antiestrogenic activity in both T47D and MCF-7 human breast cancer cells. The results in FIG. 1 show that C-phenyl and C-methylDIM alone did not induce breast cancer cell proliferation whereas in combination with 1 nM of E2, the hormone-induced proliferative response was inhibited.

FIG. 2 illustrates the potent inhibition of mammary tumor growth by C-phenylDIM in DMBA-induced Sprague-Dawley rats. The anticarcinogenic response was observed at a dose as low as 1.0 mg/kg every 2 days, and, as shown in Table 1, this was not accompanied by changes in body/organ weights on altered tissue histopathology.

The inventors have previously shown the utility and advantages of combined treatment with Ah receptor-based alkylPCDFs plus tamoxifen and other ER antagonists in the treatment of breast cancer. Both ring- and C-substituted DIMs (see FIG. 10) are also Ah receptor-based antiestrogens and exhibit antiestrogenic activity in both the breast and uterus, and thus these compounds in combination with ER antagonists such as tamoxifen can also be used in combined therapy. The combined therapy would act synergistically or additively in blocking tumor growth in the breast and also protect against potential induction of endometrial cancer by ER antagonists such as tamoxifen.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

What is claimed is:
1. A chemical compound of the formula:

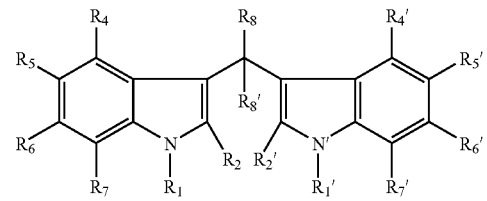

wherein:
$R_1$, $R_2$, $R_4$, $R_5$, $R_6$, $R_7$, $R_1'$, $R_2'$, $R_4'$, $R_5'$, $R_6'$, and $R_7'$ are each independently selected from the group consisting of hydrogen, a halogen, a linear alkyl group containing one to about ten carbon atoms, a branched alkyl group containing one to about ten carbon atoms, an alkoxy group containing one to about ten carbon atoms, and a nitro group;

at least one of $R_1$, $R_2$, $R_4$, $R_5$, $R_6$, $R_7$, $R_1'$, $R_2'$, $R_4'$, $R_5'$, $R_6'$, and $R_7'$ are not hydrogen;

at least one of $R_8$ and $R_8'$ is not hydrogen; and when $R_1$, $R_4$, $R_5$, $R_6$, $R_7$, $R_1'$, $R_4'$, $R_5'$, $R_6'$, and $R_7'$ are hydrogen, $R_2$, $R_2'$ and one of $R_8$ and $R_8'$ are methyl, the other one of $R_8$ and $R_8'$ is not hydrogen; provided that when:

$R_8'$ is an alkyl group of two carbons; $R_1$, $R_2$, $R_4$, $R_6$, $R_7$, $R_1'$, $R_2'$, $R_4'$, $R_6'$, $R_7'$, and $R_8$ are hydrogen; $R_5'$ is selected from the group consisting of hydrogen, chlorine, fluorine, a linear alkyl group containing one to about ten carbon atoms, a branched alkyl group containing one to about ten carbon atoms, an alkoxy group containing two to about ten carbon atoms, and a nitro group; and R5' is selected from the group consisting of chlorine, fluorine, a linear alkyl group containing one to about ten carbon atoms, a branched alkyl group containing one to about ten carbon atoms, an alkoxy group containing one to about ten carbon atoms, and a nitro group; and $R_8'$ is an alkyl group of two carbons; $R_1$, $R_2$, $R_4$, $R_6$, $R_7$, $R_1'$, $R_2'$, $R_4'$, $R_6'$, $R_7'$, and $R_8$ are hydrogen; $R_5'$ is an alkoxy group containing one carbon; $R_5$ is selected from the group consisting of halogen, a linear alkyl group containing one to about ten carbon atoms, a branched alkyl group containing one to about ten carbon atoms, an alkoxy group containing two to about ten carbon atoms, and a nitro group;

$R_2'$ is an alkyl group of one carbon; $R_1$, $R_2$, $R_4$, $R_5$, $R_6$, $R_7$, $R_1'$, $R_2'$, $R_4'$, $R_5'$, $R_6'$, $R_7'$, and $R_8$ are hydrogen; $R_8'$ is selected from the group consisting a linear alkyl group containing three to about ten carbon atoms, a branched alkyl group containing three to about ten carbon atoms, a cycloalkyl group containing three to about ten carbon atoms, and an aryl group;

$R_2'$, $R_2$, $R_8$ are each an alkyl group of one carbon; $R_1$, $R_4$, $R_5$, $R_6$, $R_7$, $R_1'$, $R_4'$, $R_5'$, $R_6'$, and $R_7'$ are hydrogen; $R_8'$ is selected from the group consisting of hydrogen, a linear alkyl group containing two to about ten carbon atoms, a branched alkyl group containing three to about ten carbon atoms, a cycloalkyl group containing three to about ten carbon atoms, and an aryl group;

$R_2'$, $R_2$, $R_8'$, $R_1$, $R_1'$, are each an alkyl group of one carbon; $R_4$, $R_5$, $R_6$, $R_7$, $R_4'$, $R_5'$, $R_6'$, and $R_7'$ are hydrogen; $R_8$ is selected from the group consisting of a linear alkyl group containing one to about ten carbon atoms, a branched alkyl group containing one to about ten carbon atoms, a cycloalkyl group containing one to about ten carbon atoms, and an aryl group;

$R_2'$, $R_2$, $R_8'$ are each an alkyl group of one carbon; $R_1$, $R_1'$, $R_4$, $R_5$, $R_6$, $R_7$, $R_4'$, $R_5'$, $R_6'$, and $R_7'$ are hydrogen; $R_8$ is selected from the group consisting of a linear alkyl group containing one to about ten carbon atoms, a branched alkyl group containing one to about ten carbon atoms, and a cycloalkyl group containing one to about ten carbon atoms;

$R_1'$, $R_1$, $R_8'$ are each an alkyl group of one carbon; $R_2$, $R_2'$, $R_4$, $R_5$, $R_6$, $R_7$, $R_4'$, $R_5'$, $R_6'$, and $R_7'$ are hydrogen; $R_8$ is selected from the group consisting of a linear alkyl group containing one to about ten carbon atoms, a branched alkyl group containing one to about ten carbon atoms, and a cycloalkyl group containing one to about ten carbon atoms;

$R_8'$ is an alkyl group of one carbon; $R_1$, $R_2$, $R_4$, $R_5$, $R_6$, $R_7$, $R_1'$, $R_4'$, $R_6'$, $R_7'$, and $R_8$ are hydrogen; $R_5'$ is an alkoxy group containing one carbon; $R_2'$ is selected from the group consisting of halogen, a linear alkyl group containing one to about ten carbon atoms, a branched alkyl group containing one to about ten carbon atoms, an alkoxy group containing two to about ten carbon atoms, and a nitro group;

$R_1$, $R_1'$, $R_8'$ are each an alkyl group of one carbon; $R_2$, $R_4$, $R_5$, $R_6$, $R_7$, $R_2'$, $R_4'$, $R_5'$, $R_6'$, and $R_7'$ are hydrogen; $R_8$ is selected from the group consisting of a hydrogen, linear alkyl group containing one to about ten carbon atoms, a branched alkyl group containing one to about ten carbon atoms, a cycloalkyl group containing one to about ten carbon atoms and an aryl group.

2. A chemical compound of the formula:

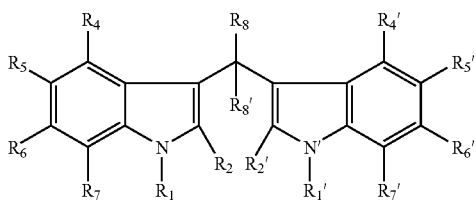

wherein:
$R_1$, $R_2$, $R_4$, $R_5$, $R_6$, $R_7$, $R_1'$, $R_2'$, $R_4'$, $R_5'$, $R_6'$, and $R_7'$ are each independently selected from the group consisting of hydrogen, a halogen, a linear alkyl group containing one to about ten carbon atoms, a branched alkyl group containing one to about ten carbon atoms, an alkoxy group containing one to about ten carbon atoms, and a nitro group;

at least one of $R_1$, $R_2$, $R_4$, $R_5$, $R_6$, $R_7$, $R_1'$, $R_2'$, $R_4'$, $R_5'$, $R_6'$, and $R_7'$ are not hydrogen;

$R_8$ and $R_8'$ are each independently selected from the group consisting of hydrogen, a linear alkyl group containing one to about ten carbon atoms, a branched alkyl group containing one to about ten carbon atoms, a cycloalkyl group containing one to about ten carbon atoms, and an aryl group;

at least one of $R_8$ and $R_8'$ is not hydrogen; provided that when $R_1$, $R_4$, $R_5$, $R_6$, $R_7$, $R_1'$, $R_4'$, $R_5'$, $R_6'$, and $R_7'$ are hydrogen, $R_2$, $R_2'$ and one of $R_8$ and $R_8'$ are methyl, the other one of $R_8$ and $R_8'$ is not hydrogen;

$R_8'$ is an alkyl group of two carbons; $R_1$, $R_2$, $R_4$, $R_6$, $R_7$, $R_1'$, $R_2'$, $R_4'$, $R_6'$, $R_7'$, and $R_8$ are hydrogen; $R_5'$ is selected from the group consisting of hydrogen, chlorine, fluorine, a linear alkyl group containing one to about ten carbon atoms, a branched alkyl group containing one to about ten carbon atoms, an alkoxy group containing two to about ten carbon atoms, and a nitro group; and R5' is selected from the group consisting of chlorine, fluorine, a linear alkyl group containing one to about ten carbon atoms, a branched alkyl group containing one to about ten carbon atoms, an alkoxy group containing one to about ten carbon atoms, and a nitro group; and $R_8'$ is an alkyl group of two carbons; $R_1$, $R_2$, $R_4$, $R_6$, $R_7$, $R_1'$, $R_2'$, $R_4'$, $R_6'$, $R_7'$, and $R_8$ are hydrogen; $R_5'$ is an alkoxy group containing one carbon; $R_5$ is selected from the group consisting of halogen, a linear alkyl group containing one to about ten carbon atoms, a branched alkyl group containing one to about ten carbon atoms, an alkoxy group containing two to about ten carbon atoms, and a nitro group;

$R_2'$ is an alkyl group of one carbon; $R_1$, $R_2$, $R_4$, $R_5$, $R_6$, $R_7$, $R_1'$, $R_2'$, $R_4'$, $R_5'$, $R_6'$, $R_7'$, and $R_8$ are hydrogen; $R_8'$ is selected from the group consisting a linear alkyl group containing three to about ten carbon atoms, a branched alkyl group containing three to about ten carbon atoms, a cycloalkyl group containing three to about ten carbon atoms, and an aryl group;

$R_2'$, $R_2$, $R_8$ are an alkyl group of one carbon; $R_1$, $R_4$, $R_5$, $R_6$, $R_7$, $R_1'$, $R_4'$, $R_5'$, $R_6'$, and $R_7'$ are hydrogen; $R_8$ is selected from the group consisting of hydrogen, a linear alkyl group containing two to about ten carbon atoms, a branched alkyl group containing three to about ten carbon atoms, a cycloalkyl group containing three to about ten carbon atoms, and an aryl group;

$R_2'$, $R_2$, $R_8'$, $R_1$, $R_1'$, are each an alkyl group of one carbon; $R_4$, $R_5$, $R_6$, $R_7$, $R_4'$, $R_5'$, $R_6'$, and $R_7'$ are hydrogen; $R_8'$ is selected from the group consisting of a linear alkyl group containing one to about ten carbon atoms, a branched alkyl group containing one to about ten carbon atoms, a cycloalkyl group containing one to about ten carbon atoms, and an aryl group;

$R_2'$, $R_2$, $R_8'$ are each an alkyl group of one carbon; $R_1$, $R_1'$, $R_4$, $R_5$, $R_6$, $R_7$, $R_4'$, $R_5'$, $R_6'$, and $R_7'$ are hydrogen; $R_8'$ is selected from the group consisting of a linear alkyl group containing one to about ten carbon atoms, a branched alkyl group containing one to about ten carbon atoms, and a cycloalkyl group containing one to about ten carbon atoms;

$R_1'$, $R_1$, $R_8'$ are each an alkyl group of one carbon; $R_2$, $R_2'$, $R_4$, $R_5$, $R_6$, $R_7$, $R_4'$, $R_5'$, $R_6'$, and $R_7'$ are hydrogen; $R_8'$ is selected from the group consisting of a linear alkyl group containing one to about ten carbon atoms, a branched alkyl group containing one to about ten carbon atoms, and a cycloalkyl group containing one to about ten carbon atoms;

$R_8'$ is an alkyl group of one carbon; $R_1$, $R_2$, $R_4$, $R_5$, $R_6$, $R_7$, $R_1'$, $R_4'$, $R_6'$, $R_7'$, and $R_8$ are hydrogen; $R_5'$ is an alkoxy group containing one carbon; $R_2'$ is selected from the group consisting of halogen, a linear alkyl group containing one to about ten carbon atoms, a branched alkyl group containing one to about ten carbon atoms, an alkoxy group containing two to about ten carbon atoms, and a nitro group;

$R_1$, $R_1'$, $R_8'$ are each an alkyl group of one carbon; $R_2$, $R_4$, $R_5$, $R_6$, $R_7$, $R_2'$, $R_4'$, $R_5'$, $R_6'$, and $R_7'$ are hydrogen; $R_8$ is selected from the group consisting of a hydrogen, linear alkyl group containing one to about ten carbon atoms, a branched alkyl group containing one to about ten carbon atoms, a cycloalkyl group containing one to about ten carbon atoms and an aryl group.

3. The chemical compound of claim 2, wherein the halogen is chlorine, bromine, or fluorine.

4. The chemical compound of claim 2, wherein:
$R_1$, $R_2$, $R_4$, $R_6$, $R_7$, $R_1'$, $R_2'$, $R_4'$, $R_6'$, and $R_7'$ are each hydrogen; and
$R_5$ and $R_5'$ are each individually a halogen.

5. The chemical compound of claim 2, wherein:
$R_1$, $R_2$, $R_4$, $R_6$, $R_7$, $R_1'$, $R_2'$, $R_4'$, $R_6'$, and $R_7'$ are each hydrogen; and
$R_5$ and $R_5'$ are each individually a linear alkyl group.

6. The chemical compound of claim 2, wherein:
$R_1$, $R_2$, $R_4$, $R_6$, $R_7$, $R_1'$, $R_2'$, $R_4'$, $R_6'$, and $R_7'$ are each hydrogen; and
$R_5$ and $R_5'$ are each individually an alkoxy group.

7. The chemical compound of claim 2, wherein:
$R_2$, $R_4$, $R_5$, $R_6$, $R_7$, $R_2'$, $R_4'$, $R_5'$, $R_6'$, and $R_7'$ are each hydrogen; and
$R_1$ and $R_1'$ are each individually an alkyl group.

8. The chemical compound of claim 2, wherein:
$R_2$, $R_4$, $R_5$, $R_6$, $R_7$, $R_2'$, $R_4'$, $R_5'$, $R_6'$, and $R_7'$ are each hydrogen; and
$R_1$ and $R_1'$ are each individually an alkoxy group.

9. The chemical compound of claim 2, wherein:
$R_1$, $R_4$, $R_5$, $R_6$, $R_7$, $R_1'$, $R_4'$, $R_5'$, $R_6'$, and $R_7'$ are each hydrogen; and
$R_2$ and $R_2'$ are each individually an alkyl group.

10. The chemical compound of claim 2, wherein:
$R_1$, $R_2$, $R_4$, $R_6$, $R_7$, $R_1'$, $R_2'$, $R_4'$, $R_6'$, and $R_7'$ are hydrogen; and
$R_5$ and $R_5'$ are each a nitro group.

11. The chemical compound of claim 2 wherein at least one of $R_8$ and $R_8'$ is a linear alkyl group.

12. The chemical compound of claim 2, wherein at least one of $R_8$ and $R_8'$ is a branched alkyl group.

13. The chemical compound of claim 2, wherein at least one of $R_8$ and $R_8'$ is a cycloalkyl group.

14. The chemical compound of claim 2, wherein at least one of $R_8$ and $R_8'$ is an aryl group.

15. The chemical compound of claim 2, wherein:
$R_1$, $R_2$, $R_1'$, and $R_2'$ are each individually hydrogen or methyl;
$R_4$, $R_5$, $R_6$, $R_7$, $R_4'$, $R_5'$, $R_6'$, and $R_7'$ are each hydrogen;
$R_8$ and $R_8'$ are each individually hydrogen, methyl, or an aryl group selected from the group consisting of $C_6H_5$, $C_6H_4OH$, $C_6H_4CH_3$, $C_6H_4CF_3$, $C_{10}H_7$, $C_6H_4C_6H_5$, and $C_6H_4OCH_3$; and
when $R_1$ and $R_1'$ are hydrogen, $R_2$, $R_2'$ and one of $R_8$ and $R_8'$ are methyl, the other one of $R_8$ and $R_8'$ is not hydrogen.

16. The chemical compound of claim 2, wherein:
$R_1$, $R_2$, $R_4$, $R_5$, $R_6$, $R_7$, $R_1'$, $R_2'$, $R_4'$, $R_5'$, $R_6'$, $R_7'$, and $R_8'$ are each hydrogen; and
$R_8$ is the aryl group p-$C_6H_4C_6H_5$.

17. The chemical compound of claim 2, wherein:
$R_1$, $R_2$, $R_4$, $R_5$, $R_6$, $R_7$, $R_1'$, $R_2'$, $R_4'$, $R_5'$, $R_6'$, $R_7'$, and $R_8'$ are each hydrogen; and
$R_8$ is the aryl group p-$C_6H_4CF_3$.

18. A composition comprising a chemical compound of the formula:

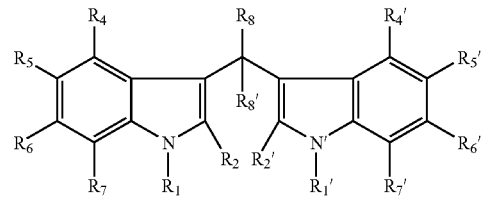

and a pharmaceutical carrier and/or diluent
wherein:
$R_1$, $R_2$, $R_4$, $R_5$, $R_6$, $R_7$, $R_1'$, $R_2'$, $R_4'$, $R_5'$, $R_6'$ and $R_7'$ are each independently selected from the group consisting of hydrogen, a halogen, a linear alkyl group containing one to about ten carbon atoms, a branched alkyl group containing one to about ten carbon atoms, an alkoxy group containing one to about ten carbon atoms, and a nitro group;
at least one of $R_1$, $R_2$, $R_4$, $R_5$, $R_6$, $R_7$, $R_1'$, $R_2'$, $R_4'$, $R_5'$, $R_6'$, and $R_7'$ are not hydrogen;
at least one of $R_8$ and $R_8'$ is not hydrogen; provided that when
$R_1$, $R_4$, $R_5$, $R_6$, $R_7$, $R_1'$, $R_4'$, $R_5'$, $R_6'$, and $R_7'$ are hydrogen, $R_2$, $R_2'$ and one of $R_8$ and $R_8'$ are methyl, the other one of $R_8$ and $R_8'$ is not hydrogen;
$R_8'$ is an alkyl group of two carbons; $R_1$, $R_2$, $R_4$, $R_6$, $R_7$, $R_1'$, $R_2'$, $R_4'$, $R_6'$, $R_7'$, and $R_8$ are hydrogen; $R_5'$ is selected from the group consisting of hydrogen, chlorine, fluorine, a linear alkyl group containing one to about ten carbon atoms, a branched alkyl group containing one to about ten carbon atoms, an alkoxy group containing two to about ten carbon atoms, and a nitro group; and R5' is selected from the group consisting of chlorine, fluorine, a linear alkyl group containing one to about ten carbon atoms, a branched alkyl group containing one to about ten carbon atoms, an alkoxy group containing one to about ten carbon atoms, and a nitro group; and
$R_8'$ is an alkyl group of two carbons; $R_1$, $R_2$, $R_4$, $R_6$, $R_7$, $R_1'$, $R_2'$, $R_4'$, $R_6'$, $R_7'$, and $R_8$ are hydrogen; $R_5'$ is an alkoxy group containing one carbon; $R_5$ is selected from the group consisting of halogen, a linear alkyl group containing one to about ten carbon atoms, a branched alkyl group containing one to about ten carbon atoms, an alkoxy group containing two to about ten carbon atoms, and a nitro group;
$R_2'$ is an alkyl group of one carbon; $R_1$, $R_2$, $R_4$, $R_5$, $R_6$, $R_7$, $R_1'$, $R_2'$, $R_4'$, $R_5'$, $R_6'$, $R_7'$, and $R_8$ are hydrogen; $R_8'$ is selected from the group consisting a linear alkyl group containing three to about ten carbon atoms, a branched alkyl group containing three to about ten carbon atoms, a cycloalkyl group containing three to about ten carbon atoms, and an aryl group;
$R_2'$, $R_2$, $R_8$ are each an alkyl group of one carbon; $R_1$, $R_4$, $R_5$, $R_6$, $R_7$, $R_1'$, $R_4'$, $R_5'$, $R_6'$, and $R_7'$ are hydrogen; $R_8'$ is selected from the group consisting of hydrogen, a linear alkyl group containing two to about ten carbon atoms, a branched alkyl group containing three to about ten carbon atoms, a cycloalkyl group containing three to about ten carbon atoms, and an aryl group;
$R_2'$, $R_2$, $R_8'$, $R_1$, $R_1'$, are each an alkyl group of one carbon; $R_4$, $R_5$, $R_6$, $R_7$, $R_4'$, $R_5'$, $R_6'$, and $R_7'$ are hydrogen; $R_8'$ is selected from the group consisting of a linear alkyl group containing one to about ten carbon atoms, a branched alkyl group containing one to about ten carbon atoms, a cycloalkyl group containing one to about ten carbon atoms, and an aryl group;

$R_2'$, $R_2$, $R_8'$ are each an alkyl group of one carbon; $R_1$, $R_1'$, $R_4$, $R_5$, $R_6$, $R_7$, $R_4'$, $R_5'$, $R_6'$, and $R_7'$ are hydrogen; $R_8'$ is selected from the group consisting of a linear alkyl group containing one to about ten carbon atoms, a branched alkyl group containing one to about ten carbon atoms, and a cycloalkyl group containing one to about ten carbon atoms;

$R_1'$, $R_1$, $R_8'$ are each an alkyl group of one carbon; $R_2$, $R_2'$, $R_4$, $R_5$, $R_6$, $R_7$, $R_4'$, $R_5'$, $R_6'$, and $R_7'$ are hydrogen; $R_8'$ is selected from the group consisting of a linear alkyl group containing one to about ten carbon atoms, a branched alkyl group containing one to about ten carbon atoms, and a cycloalkyl group containing one to about ten carbon atoms;

$R_8'$ is an alkyl group of one carbon; $R_1$, $R_2$, $R_4$, $R_5$, $R_6$, $R_7$, $R_1'$, $R_4'$, $R_6'$, $R_7'$, and $R_8$ are hydrogen; $R_5'$ is an alkoxy group containing one carbon; $R_2'$ is selected from the group consisting of halogen, a linear alkyl group containing one to about ten carbon atoms, a branched alkyl group containing one to about ten carbon atoms, an alkoxy group containing two to about ten carbon atoms, and a nitro group;

$R_1$, $R_1'$, $R_8'$ are each an alkyl group of one carbon; $R_2$, $R_4$, $R_5$, $R_6$, $R_7$, $R_2'$, $R_4'$, $R_5'$, $R_6'$, and $R_7'$ are hydrogen; $R_8$ is selected from the group consisting of a hydrogen, linear alkyl group containing one to about ten carbon atoms, a branched alkyl group containing one to about ten carbon atoms, a cycloalkyl group containing one to about ten carbon atoms and an aryl group.

19. A composition comprising a chemical compound of the formula:

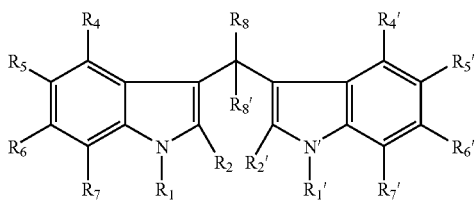

and a pharmaceutical carrier and/or diluent,
wherein:

$R_1$, $R_2$, $R_4$, $R_5$, $R_6$, $R_7$, $R_1'$, $R_2'$, $R_4'$, $R_5'$, $R_6'$, and $R_7'$ are each independently selected from the group consisting of hydrogen, a halogen, a linear alkyl group containing one to about ten carbon atoms, a branched alkyl group containing one to about ten carbon atoms, an alkoxy group containing one to about ten carbon atoms, and a nitro group;

at least one of $R_1$, $R_2$, $R_4$, $R_5$, $R_6$, $R_7$, $R_1'$, $R_2'$, $R_4'$, $R_5'$, and $R_7'$ are not hydrogen;

$R_8$ and $R_8'$ are each independently selected from the group consisting of hydrogen, a linear alkyl group containing one to about ten carbon atoms, a branched alkyl group containing one to about ten carbon atoms, a cycloalkyl group containing one to about ten carbon atoms, and an aryl group;

at least one of $R_8$ and $R_8'$ is not hydrogen, provided that when $R_1$, $R_4$, $R_5$, $R_6$, $R_7$, $R_1'$, $R_4'$, $R_5'$, $R_6'$, and $R_7'$ are hydrogen, $R_2$, $R_2'$ and one of $R_8$ and $R_8'$ are methyl, the other one of $R_8$ and $R_8'$ is not hydrogen;

$R_8'$ is an alkyl group of two carbons; $R_1$, $R_2$, $R_4$, $R_6$, $R_7$, $R_1'$, $R_2'$, $R_4'$, $R_6'$, $R_7'$, and $R_8$ are hydrogen; $R_5'$ is selected from the group consisting of hydrogen, chlorine, fluorine, a linear alkyl group containing one to about ten carbon atoms, a branched alkyl group containing one to about ten carbon atoms, an alkoxy group containing two to about ten carbon atoms, and a nitro group; and $R_5'$ is selected from the group consisting of chlorine, fluorine, a linear alkyl group containing one to about ten carbon atoms, a branched alkyl group containing one to about ten carbon atoms, an alkoxy group containing one to about ten carbon atoms, and a nitro group; and $R_8'$ is an alkyl group of two carbons; $R_1$, $R_2$, $R_4$, $R_6$, $R_7$, $R_1'$, $R_2'$, $R_4'$, $R_6'$, $R_7'$, and $R_8$ are hydrogen; $R_5'$ is an alkoxy group containing one carbon; $R_5$ is selected from the group consisting of halogen, a linear alkyl group containing one to about ten carbon atoms, a branched alkyl group containing one to about ten carbon atoms, an alkoxy group containing two to about ten carbon atoms, and a nitro group;

$R_2'$ is an alkyl group of one carbon; $R_1$, $R_2$, $R_4$, $R_5$, $R_6$, $R_7$, $R_1'$, $R_2'$, $R_4'$, $R_5'$, $R_6'$, $R_7'$, and $R_8$ are hydrogen; $R_8'$ is selected from the group consisting a linear alkyl group containing one to about ten carbon atoms, a branched alkyl group containing three to about ten carbon atoms, a cycloalkyl group containing one to about ten carbon atoms, and an aryl group;

$R_2'$, $R_2$, $R_8$ are each an alkyl group of one carbon; $R_1$, $R_4$, $R_5$, $R_6$, $R_7$, $R_1'$, $R_4'$, $R_5'$, $R_6'$, and $R_7'$ are hydrogen; $R_8'$ is selected from the group consisting of hydrogen, a linear alkyl group containing two to about ten carbon atoms, a branched alkyl group containing three to about ten carbon atoms, a cycloalkyl group containing three to about ten carbon atoms, and an aryl group;

$R_2'$, $R_2$, $R_8'$, $R_1$, $R_1'$ are each an alkyl group of one carbon; $R_4$, $R_5$, $R_6$, $R_7$, $R_4'$, $R_5'$, $R_6'$, and $R_7'$ are hydrogen; $R_8'$ is selected from the group consisting of a linear alkyl group containing one to about ten carbon atoms, a branched alkyl group containing one to about ten carbon atoms, a cycloalkyl group containing one to about ten carbon atoms, and an aryl group;

$R_2'$, $R_2$, $R_8'$ are each an alkyl group of one carbon; $R_1$, $R_1'$, $R_4$, $R_5$, $R_6$, $R_7$, $R_4'$, $R_5'$, $R_6'$, and $R_7'$ are hydrogen; $R_8'$ is selected from the group consisting of a linear alkyl group containing one to about ten carbon atoms, a branched alkyl group containing one to about ten carbon atoms, and a cycloalkyl group containing one to about ten carbon atoms;

$R_1'$, $R_1$, $R_8'$ are each an alkyl group of one carbon; $R_2$, $R_2'$, $R_4$, $R_5$, $R_6$, $R_7$, $R_4'$, $R_5'$, $R_6'$, and $R_7'$ are hydrogen; $R_8'$ is selected from the group consisting of a linear alkyl group containing one to about ten carbon atoms, a branched alkyl group containing one to about ten carbon atoms, and a cycloalkyl group containing one to about ten carbon atoms;

$R_8'$ is an alkyl group of two carbons; $R_1$, $R_2$, $R_4$, $R_5$, $R_6$, $R_7$, $R_1'$, $R_4'$, $R_6'$, $R_7'$, and $R_8$ are hydrogen; $R_5'$ is an alkoxy group containing one carbon; $R_5$ is selected from the group consisting of halogen, a linear alkyl group containing one to about ten carbon atoms, a branched alkyl group containing one to about ten carbon atoms, an alkoxy group containing two to about ten carbon atoms, and a nitro group;

$R_1$, $R_1'$, $R_8'$ are each an alkyl group of one carbon; $R_2$, $R_4$, $R_5$, $R_6$, $R_7$, $R_2'$, $R_4'$, $R_5'$, $R_6'$, and $R_7'$ are hydrogen; $R_8$ is selected from the group consisting of a hydrogen, linear alkyl group containing one to about ten carbon atoms, a branched alkyl group containing one to about ten carbon atoms, a cycloalkyl group containing one to about ten carbon atoms and an aryl group.

20. The composition of claim 19, wherein the halogen is chlorine, bromine, or fluorine.

21. The composition of claim 19, wherein:
    $R_1$, $R_2$, $R_4$, $R_6$, $R_7$, $R_1'$, $R_2'$, $R_4'$, $R_6'$, and $R_7'$ are each hydrogen; and
    $R_5$ and $R_5'$ are each individually a halogen.

22. The composition of claim 19, wherein:
    $R_1$, $R_2$, $R_4$, $R_6$, $R_7$, $R_1'$, $R_2'$, $R_4'$, $R_6'$, and $R_7'$ are each hydrogen; and
    $R_5$ and $R_5'$ are each individually a linear alkyl group.

23. The composition of claim 19, wherein:
    $R_1$, $R_2$, $R_4$, $R_6$, $R_7$, $R_1'$, $R_2'$, $R_4'$, $R_6'$, and $R_7'$ are each hydrogen; and
    $R_5$ and $R_5'$ are each individually an alkoxy group.

24. The composition of claim 19, wherein:
    $R_2$, $R_4$, $R_5$, $R_6$, $R_7$, $R_2'$, $R_4'$, $R_5'$, $R_6'$, and $R_7'$ are each hydrogen; and
    $R_1$ and $R_1'$ are each individually an alkyl group.

25. The composition of claim 19, wherein:
    $R_2$, $R_4$, $R_5$, $R_6$, $R_7$, $R_2'$, $R_4'$, $R_5'$, $R_6'$, and $R_7'$ are each hydrogen; and
    $R_1$ and $R_1'$ are each individually an alkoxy group.

26. The composition of claim 19, wherein:
    $R_1$, $R_4$, $R_5$, $R_6$, $R_7$, $R_1'$, $R_4'$, $R_5'$, $R_6'$, and $R_7'$ are each hydrogen; and
    $R_2$ and $R_2'$ are each individually an alkyl group.

27. The composition of claim 19, wherein:
    $R_1$, $R_2$, $R_4$, $R_6$, $R_7$, $R_1'$, $R_2'$, $R_4'$, $R_6'$, and $R_7'$ are hydrogen; and
    $R_5$ and $R_5'$ are each a nitro group.

28. The composition of claim 19, wherein at least one of $R_8$ and $R_8'$ is a linear alkyl group.

29. The composition of claim 19, wherein at least one of $R_8$ and $R_8'$ is a branched alkyl group.

30. The composition of claim 19, wherein at least one of $R_8$ and $R_8'$ is a cycloalkyl group.

31. The composition of claim 19, wherein at least one of $R_8$ and $R_8'$ is an aryl group.

32. The composition of claim 19, wherein:
    $R_1$, $R_2$, $R_1'$, and $R_2'$ are each individually hydrogen or methyl;
    $R_4$, $R_5$, $R_6$, $R_7$, $R_4'$, $R_5'$, $R_6'$, and $R_7'$ are each hydrogen;
    $R_8$ and $R_8'$ are each individually hydrogen, methyl, or an aryl group selected from the group consisting of $C_6H_5$, $C_6H_4OH$, $C_6H_4CH_3$, $C_6H_4CF_3$, $C_{10}H_7$, $C_6H_4C_6H_5$, and $C_6H_4OCH_3$; and
    when $R_1$ and $R_1'$ are hydrogen, $R_2$, $R_2'$ and one of $R_8$ and $R_8'$ are methyl, the other one of $R_8$ and $R_8'$ is not hydrogen.

33. The composition of claim 19, wherein:
    $R_1$, $R_2$, $R_4$, $R_5$, $R_6$, $R_7$, $R_1'$, $R_2'$, $R_4'$, $R_5'$, $R_6'$, $R_7'$, and $R_8'$ are each hydrogen; and
    $R_8$ is the aryl group p-$C_6H_4C_6H_5$.

34. The composition of claim 19, wherein:
    $R_1$, $R_2$, $R_4$, $R_5$, $R_6$, $R_7$, $R_1'$, $R_2'$, $R_4'$, $R_5'$, $R_6'$, $R_7'$, and $R_8'$ are each hydrogen; and
    $R_8$ is the aryl group p-$C_6H_4CF_3$.

* * * * *